United States Patent
Walker et al.

(10) Patent No.: US 12,063,318 B2
(45) Date of Patent: Aug. 13, 2024

(54) MEDICAL INJECTORS AND SYSTEMS AND METHODS FOR AN INJECTION MANAGEMENT PLATFORM

(71) Applicant: Koska Family Limited, East Sussex (GB)

(72) Inventors: Jay S. Walker, Stamford, CT (US); Timothy Scott Case, Washington, DC (US); Lindsey Walker, Stamford, CT (US); Isra Elmahdi, Washington, DC (US); Daniel Curaca Malito, Arlington, VA (US); Kristen Marie Hannon, Eldersburg, MD (US)

(*) Notice: Subject to any disclaimer, the term of this patent is extended or adjusted under 35 U.S.C. 154(b) by 0 days.

(21) Appl. No.: 18/051,187

(22) Filed: Oct. 31, 2022

(65) Prior Publication Data
US 2023/0081577 A1  Mar. 16, 2023

Related U.S. Application Data

(63) Continuation of application No. PCT/US2021/030530, filed on May 3, 2021.

(60) Provisional application No. 63/019,192, filed on May 1, 2020.

(51) Int. Cl.
*H04L 9/00* (2022.01)
*G16H 10/60* (2018.01)

(52) U.S. Cl.
CPC ............. *H04L 9/50* (2022.05); *G16H 10/60* (2018.01); *G06Q 2220/00* (2013.01)

(58) Field of Classification Search
CPC ......... H04L 9/00; H04L 9/3226; G16H 10/60; G16H 10/65; G16H 40/67; G16H 20/17; G06Q 2220/00

USPC .................................................. 340/5.8, 5.81
See application file for complete search history.

(56) References Cited

U.S. PATENT DOCUMENTS

| | | | |
|---|---|---|---|
| 10,398,524 B2* | 9/2019 | Denny | A61M 5/20 |
| 10,902,955 B1* | 1/2021 | Federoff | G16H 50/30 |
| 10,949,217 B1* | 3/2021 | Nitsopoulos | G06F 9/45558 |
| 10,991,190 B1* | 4/2021 | Luthra | G07C 9/27 |
| 2002/0087362 A1 | 7/2002 | Cobb et al. | |

(Continued)

FOREIGN PATENT DOCUMENTS

| | | |
|---|---|---|
| WO | WO 2018/020382 | 2/2018 |
| WO | WO 2018/124501 | 7/2018 |
| WO | 2019154600 | 8/2019 |

OTHER PUBLICATIONS

Supplemental European Search Report for 21796025.1 dated May 22, 2024; 7 pps.

*Primary Examiner* — Nam V Nguyen
(74) *Attorney, Agent, or Firm* — RowanTree Law Group, PLLC; Magdalena M. Fincham

(57) ABSTRACT

Systems, methods and articles of manufacture provide for an injection management platform that allows the verification and management of injection event transactions involving injectors equipped with NFC or RFID chips utilizing a distributed and secure technology such as blockchain. An injection event transaction ledger allows for digital receipts of injection event transactions to be securely verified and updated. In accordance with some embodiments, injectors may comprise blow-fill-seal (BFS) injectors that are pre-filled with a single dose of a fluid agent comprising a vaccine or medicament, allowing for tracking of individual doses of the fluid agent via the injection event transaction ledger.

13 Claims, 10 Drawing Sheets

(56) References Cited

U.S. PATENT DOCUMENTS

| | | | |
|---|---|---|---|
| 2006/0264778 A1* | 11/2006 | Lim | A61M 1/0281 |
| | | | 600/576 |
| 2015/0093735 A1* | 4/2015 | Smith | G09B 23/00 |
| | | | 434/276 |
| 2016/0063215 A1 | 3/2016 | Zamer | |
| 2016/0246943 A1 | 8/2016 | Lake | |
| 2018/0075202 A1 | 3/2018 | David et al. | |
| 2018/0197143 A1 | 7/2018 | Daub | |
| 2019/0156931 A1 | 5/2019 | Skoda | |
| 2019/0214116 A1 | 7/2019 | Eberting | |
| 2020/0118164 A1 | 4/2020 | Defrank | |
| 2023/0081577 A1 | 3/2023 | Walker et al. | |

\* cited by examiner

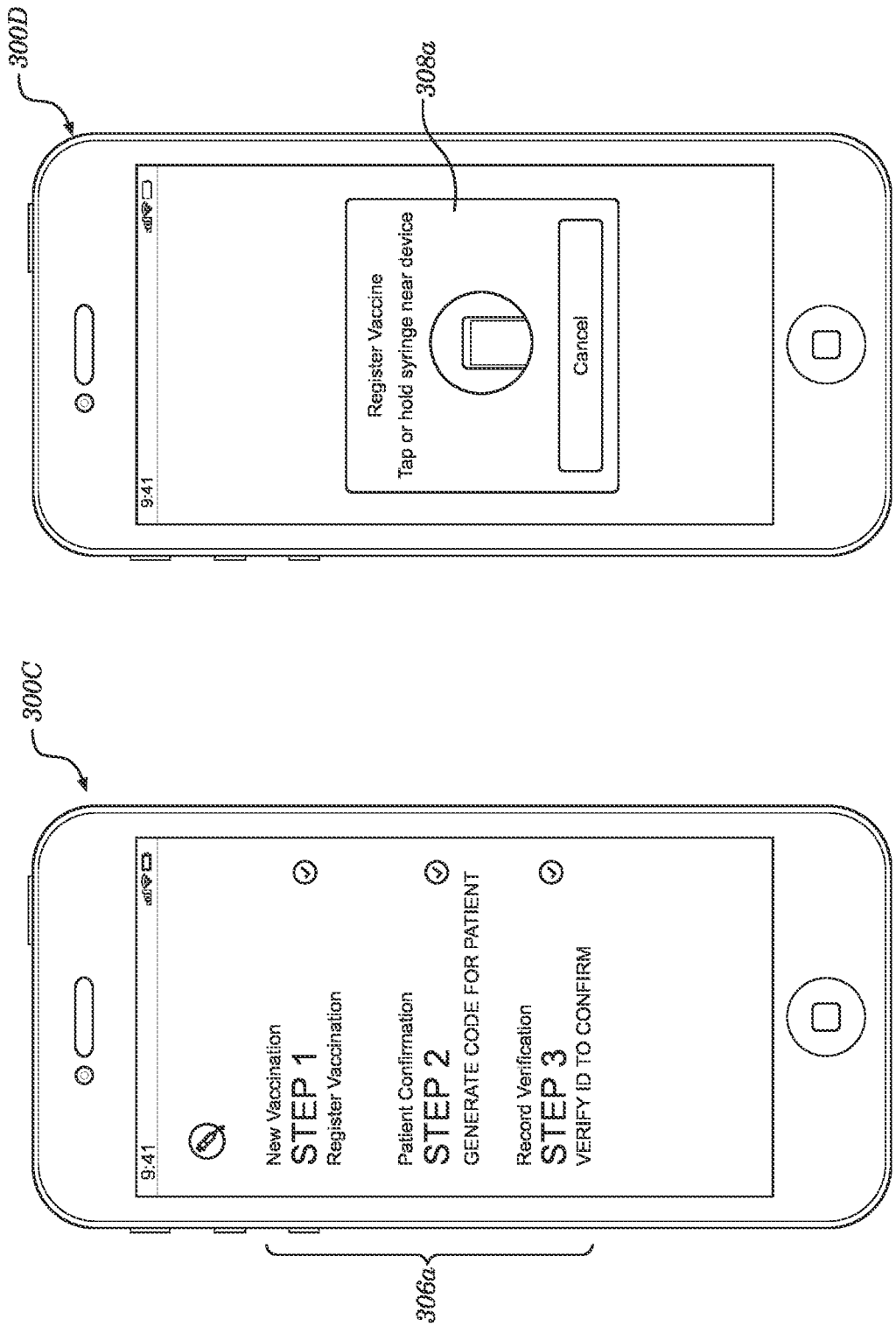

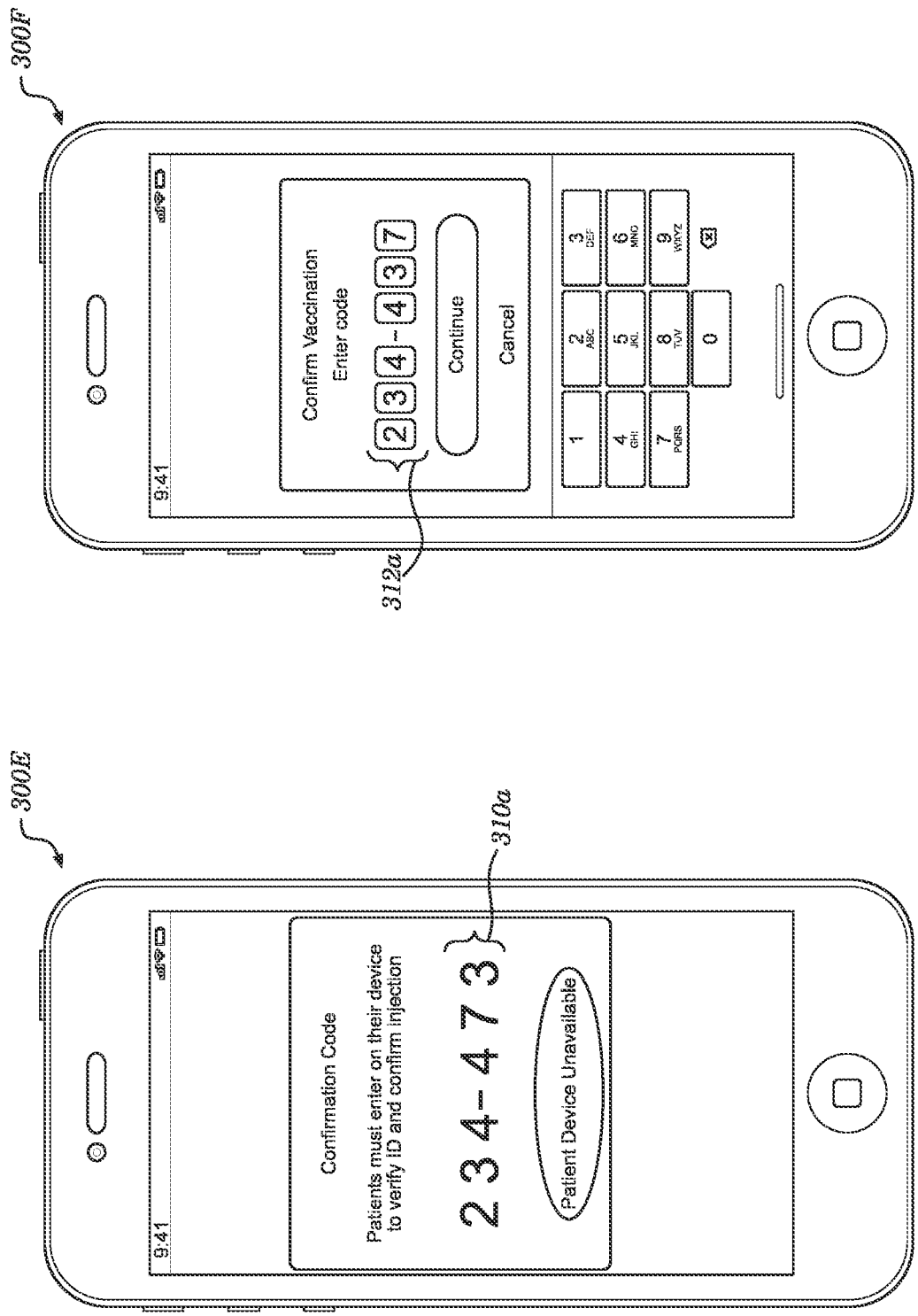

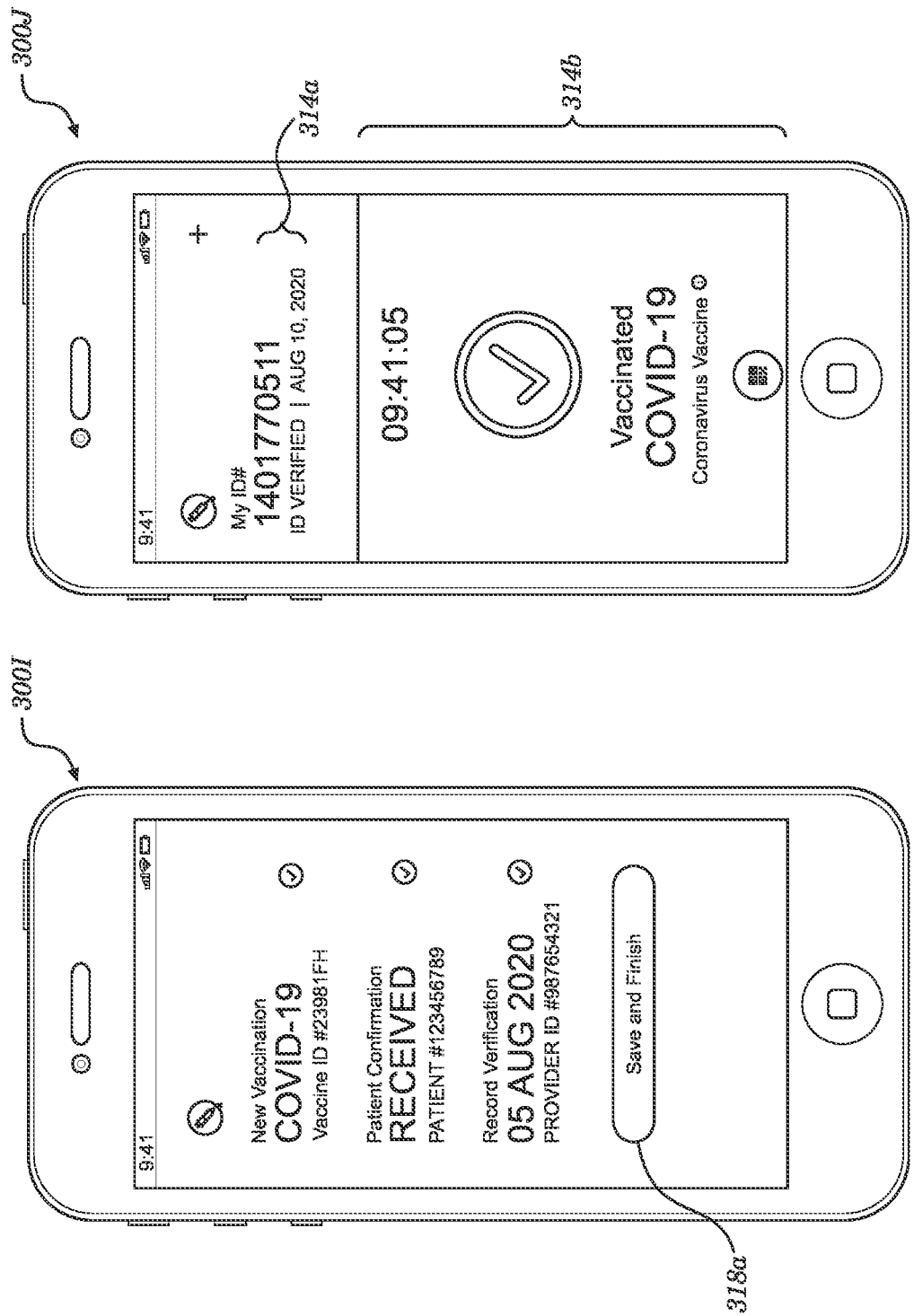

MEDICAL INJECTORS AND SYSTEMS AND METHODS FOR AN INJECTION MANAGEMENT PLATFORM

CLAIM OF PRIORITY

The present application is a Continuation Application of PCT Application No. PCT/US21/30530, filed May 3, 2021 in the name of Walker et al. and titled MEDICAL INJECTORS AND SYSTEMS AND METHODS FOR AN INJECTION MANAGEMENT PLATFORM; this PCT Application No. PCT/US21/30530 claims the benefit of U.S. Provisional Application No. 63/019,192 filed in the name of Walker et al. on May 1, 2020 and titled NFC-ENABLED DRUG CONTAINING SYSTEM AND ASSOCIATED INFORMATION LAYER. The entirety of each of these Applications is incorporated by reference herein for all purposes.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Every year, staggering numbers of people become infected and die from a variety of diseases, some of which are preventable (or the severity of which could have been mitigated) through injectable medicines (i.e., medicines delivered via use of a syringe or other needle-type medical delivery device). Although injectable medicines have led to a dramatic decline in the number of cases of several infectious diseases (or the severity of symptoms or instances of death resulting therefrom), some of these diseases remain quite common and new ones are emerging. In many instances, large populations of the world, particularly in developing or economically disadvantaged countries, suffer from the spread of preventable diseases due to ineffective injectable medicine/vaccine delivery programs, either because of poor implementation, lack of available medicines/vaccines, lack of sufficient skilled persons to administer injections, poor tracking and management of where injections have been administered vs. where there is still a need for administration, or combinations thereof.

More recent world events, such as the COVID-19 Pandemic, have further highlighted the inadequacies of existing vaccine and other injectable medicine administration programs. This Pandemic is an example of a situation in which a populace would benefit from (i) being able to verifiably and efficiently track who has been vaccinated (as well as perhaps tracking where, when and with what particular vaccine); (ii) allowing persons to efficiently provide evidence of having been vaccinated (and, in some embodiments, a current vaccination status, such as for circumstances in which vaccine effectiveness requires booster shots or additional injections), (iii) identifying areas of the population that have ongoing vaccination needs; and/or (iv) enabling a wider-ranging vaccination effort by providing means for less skilled persons to administer vaccinations. Existing systems and infrastructure have proven inadequate to satisfy the foregoing needs.

BRIEF DESCRIPTION OF THE DRAWINGS

An understanding of embodiments described herein and many of the attendant advantages thereof may be readily obtained by reference to the following detailed description when considered with the accompanying drawings, wherein:

FIGS. 3A through 3L are example graphical user interfaces of a mobile device App that may be output to users in accordance with some embodiments described herein;

DETAILED DESCRIPTION

Figure 1:
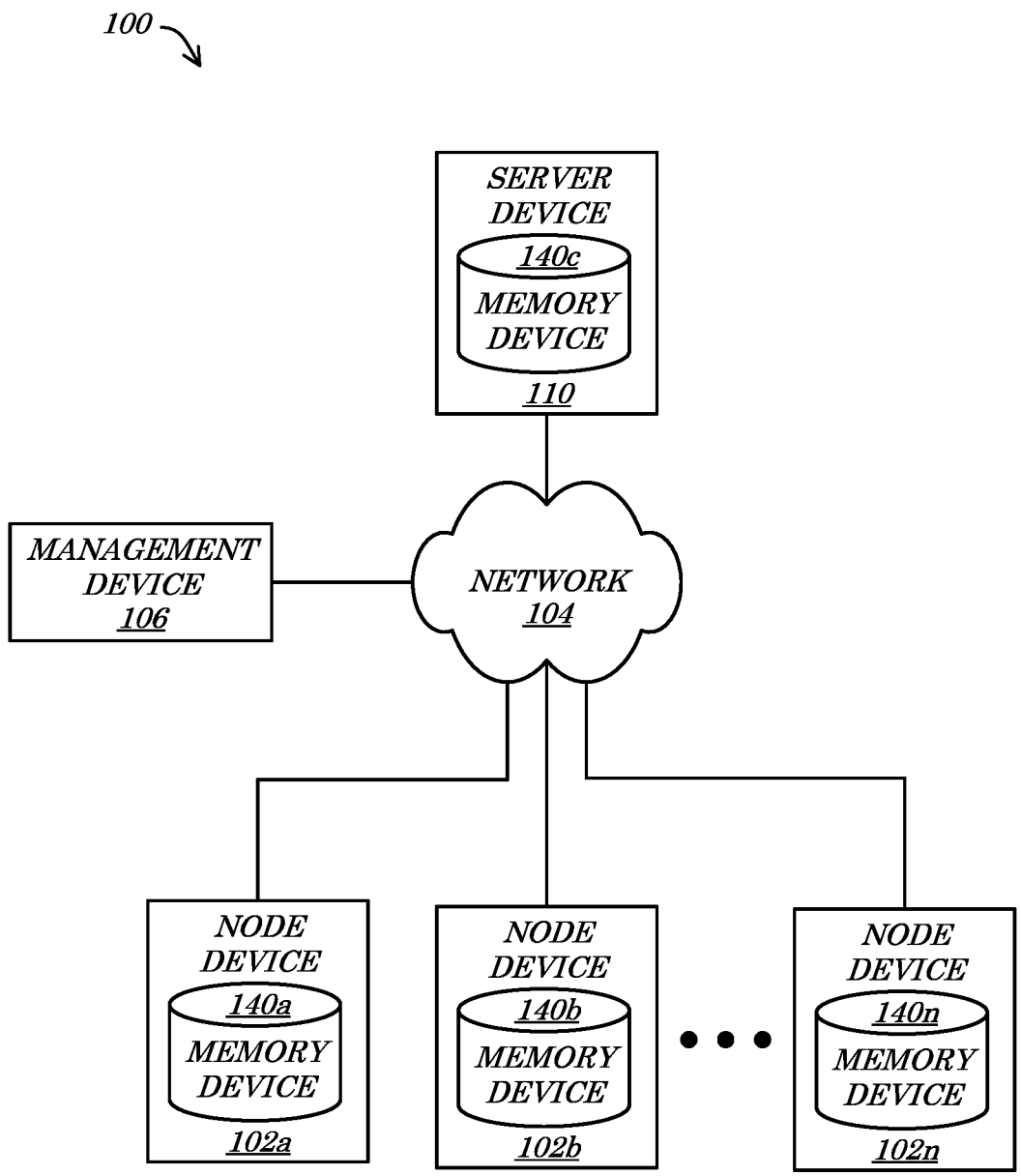
FIG. 1 is an example block diagram of a system consistent with at least some embodiments described herein.

Embodiments described herein relate to injectors for administering single doses of fluid agents that are equipped with a data storage mechanism that allows for electronically recognizing, tracking and/or authorizing the administration of the single doses into patient. In some embodiments, an electronic platform is operable to facilitate (i) transmission of data from an injector to an injection provider device and then to the electronic processing system of the platform, to facilitate the authorization and tracking of the administration of a dose of the fluid agent from the injector into a patient; and/or (ii) exchange of data with a patient's device that allows the patient to receive and store a digital receipt of having had the single dose of the fluid agent administered from the injector. The electronic platform further allows for healthcare systems and authorities to generate and utilize an information layer associated with the injectors that are equipped with the data mechanism.

An injector, as the term is used herein, refers to a device that is filled with a single dose of a fluid agent, such as a vaccine or medicament (which may, in some embodiments, include a lyophilized component that may be reconstituted into a fluid prior to injection). An injector may be made of plastic, glass or another material and the embodiments described herein are not dependent on an injector being made from any particular material. An injector may comprise, for example, an auto-injector that is spring loaded or has another mechanism for assisting with the injection of the fluid agent, or a manual injector that relies on the user to operate the injection mechanism. Examples of manual injectors include plunger-type syringes or plastic vial injectors (such as blow-fill-seal ("BFS") injectors) that requires a pressure or squeezing action on the part of the injection provider (e.g., a nurse or the patient, in the case of self-administered injections) in order to squeeze or otherwise force the fluid agent out of the vial or other component comprising the injector for containing the fluid agent. Examples of an injector device that may be utilized in embodiments described herein can be found in PCT Application No. PCT/US21/25683 filed on Apr. 3, 2021 in the name of Koska et al. and entitled SYSTEMS AND METHODS FOR PRE-FILLED MEDICAL DELIVERY DEVICES and in PCT Application No. PCT/US18/61696, filed on Nov. 16, 2018 in the name of Koska et al. and entitled SYSTEMS AND METHODS FOR FLUID DELIV- ERY MANIFOLDS, each of which PCT applications are incorporated by reference herein for all purposes.

It should be noted that injectors that are pre-filled with single doses of a fluid agent may be pre-filled during a manufacturing process (pre-filled), such as the BFS injectors described in the afore-referenced PCT applications to Koska et al., or filled by injection provider, such as by extracting a single dose from a multi-dose container (field-filled). Injectors that are field-filled or field-fillable are ones in which an injection provider extracts a single dose of the liquid agent from another container (e.g., a multi-dose glass vial) into the injector prior to administering the injection. In the field-filled injectors, a dose of the liquid agent administered via the injector is not unique to the injector and thus an injection provider may need to provide two pieces of data to identify both the injector and an identifier of the multi-dose vial from which the dose was extracted. In a pre-filled injector, a unique identifier of the injector inherently identifies both the injector itself and the dose of the fluid agent contained therein. Identifying a dose of fluid agent may be desirable, for example, in embodiments in which information such as the batch number, type of fluid agent, manufacturer, date of manufacture of the dose, etc. are of interest. The embodiments described herein are primarily focused on pre-filled injectors in which the unique identifier In accordance with embodiments described herein, injectors are equipped with data storage mechanisms that uniquely identify each injector, such as by storing a unique identifier for each injector that is generated at the time the injector is manufactured (and, in the case of pre-filled injectors, at the time the injector is pre-filled with a dose of fluid agent). Such data storage mechanisms may comprise, for example, a Near Field Communication (NFC) chip, a Radio Frequency Identification (RFID) chip, a QR code, a bar code or any other machine-readable mechanism that allows for a unique identifier of an injector to be stored in association with the injector (e.g., attached to, or embedded in, the injector or a portion thereof, such as on or underneath a label on a label-portion of the injector).

It should be noted that in some embodiments, the unique identifier and/or other data stored on an NFC chip or other data storage mechanism may be stored in encrypted form. It should further be noted that, in some embodiments, communications with the NFC chip (or other data storage mechanism) and/or the Injection Management App may be done in an encrypted form (e.g., using public key-private key protocols) or utilizing other security measures (e.g., dual factor authentication or blockchain technology).

In accordance with some embodiments, an Injection Management System may comprise providing an Injection Management App for facilitating the verification/authorization of injections via injectors equipped with data storage mechanisms as described herein. An Injection Management App may be utilized by individuals to communicate with a centralized or decentralized (e.g., blockchain-based) system for facilitating the creation and utilization of an information layer or electronic record keeping based on use of the injectors. In accordance with some embodiments, the Injection Management App may include an injection provider portal or platform, via which injection providers or other individuals who administer injections of fluid agents using injectors as described herein ("injection providers") may sign in to the system and obtain access to functionality for such injection providers. For example, an injection provider may utilize the Injection Management App to confirm that a particular dose in a pre-filled injectors is valid and authorized for use (e.g., not counterfeit, not expired, and not subject to a recall), prior to administering it to a patient, and to record with the Injection Management System each injection event comprising an instance of the injection provider having provided a dose of a fluid agent packaged in a uniquely identified injector to a particular patient. Similarly, the Injection management App may include a patient portal or platform, via which individuals receiving injections ("patients") may sign in to the system to access functionality for patients (e.g., obtaining a digital receipt, to be stored on a mobile device of the patient, that can be shared in some form with third parties to offer verification of having been vaccinated with a particular vaccine or otherwise having received a dose of a particular fluid agent).

In some embodiments and circumstances, a given individual may serve as both an injection provider and a patient. In some embodiments, a given individual may serve as both an injection provider and a patient for a given injection event (e.g., the individual can self-administer an injection).

Applicant notes that utilizing a pre-filled injector that is uniquely identifiable and providing an Injection Management App that is operable to recognize an injection event in which the injector is utilized offers one or more advantages over existing capabilities of healthcare systems. For example, many implementations of immunization programs generally include administration of vaccines via a typical reusable syringe. However, in many situations, particularly in developing countries, the administration of vaccines occur outside of a hospital and may be provided by a non-professional, such that injections are given to patients without carefully controlling access to syringes. The use of reusable syringes under those circumstances increases the risk of infection and spread of blood-borne diseases, particularly when syringes, which have been previously used and are no longer sterile, are used to administer subsequent injections. For example, the World Health Organization (WHO) estimates that blood-borne diseases, such as Hepatitis and human immunodeficiency virus (HIV), are being transmitted due to reuse of such syringes, resulting the death of more than one million people each year. Utilizing a pre-filled injector that is equipped with a unique identifier, and particularly with providing an easy-to-use Injection Management App that tracks when a particular injector has been utilized and, in accordance with some embodiments, outputs a warning or withholds authorization of an administration of a dose of a fluid agent from a particular injector more than once, would help alleviate such drawbacks to existing systems.

Embodiments presented herein are descriptive of systems, apparatus, interfaces, methods, and articles of manufacture for managing, tracking, authorizing and verifying injection events in which a patient receives an injection of a dose of fluid agent from an injector that is equipped with a unique identifier. In some embodiments, for example, an injection management system (which may, in some embodiments, incorporate a blockchain distributed network system for security purposes) facilitates a method which provides for (i) recognizing a first injection event transaction, wherein the recognizing is based on receiving, via an injection provider platform of an Injection Management App stored on a first mobile device corresponding to first user, an indication of a dose of a fluid agent to be administered to a patient, the indication including first data comprising a unique identifier of an injector containing the dose, wherein the first user previously signed in to the injection provider platform via the first mobile device by providing first user credentials that allowed the electronic processing device to uniquely identify the first user and recognize the first user as a registered injection provider; (ii) authorizing, based on the unique identifier of the injector, the dose of the fluid agent; (iii) generating an electronic record unique to the first injection event transaction, thereby generating a first injection event record; (iv) receiving, from the first user and via the Injection Management App, an indication that the dose has been administered to the patient; (v) generating, in response to the receiving, a first passcode, the first passcode corresponding to an expiration time of the first passcode and being stored in association with the first injection event record; (vi) outputting the first passcode to the first user via the Injection Management App; (vii) receiving, from a second user and prior to the expiration time, the first passcode, wherein the second user has previously signed in to a patient platform of the Injection Management App via a second mobile device by providing second user credentials that allowed the electronic processing device to uniquely identify the second user and recognize the second user as a registered patient; (viii) concluding, based on the receiving of the first passcode from the second user, that the second user is the patient to whom the dose of the fluid agent from the injector has been administered by the first user as part of the first injection event transaction; (ix) updating the first injection event record to indicate that the dose of the fluid agent has been administered to the second user; and (x) transmitting to the second mobile device of the second user, via the patient portal of the Injection Management App, a verifiable confirmation that the dose of the fluid agent has been administered to the second user, thereby transmitting to the second mobile device a digital receipt for the first injection event, to be stored in the patient portal of the Injection Management App of the second user.

Applicant describes herein various improvements that can be made to injectors such as BFS vials or a traditional glass vials by including within, or attaching to, the injector a unique identifier. The unique identifier may be in the form of a physical component such as an NFC or RFID chip, or a QR code. Irrespective of the form in which the unique identifier is embodied, the presence of the unique identifier as being associated with each injector allows for a layer of information to be created around, or associated with, the injector (or the dose contained within the injector, particularly in the case of pre-filled injectors) and/or a patient who receives an injection of a dose of the fluid agent packaged in the injector. Although various embodiments are described herein as being applicable to an injector comprising a BFS vial injector, it should be understood that at least some of these embodiments may also be applied to a glass or other vial or syringe system that can benefit from the generation of data and new functionalities described herein. Thus, it should be understood that when reference is made to a BFS vial or other particular type of injector, that references it not intended to be limiting and in various embodiments the same or similar functionality may be provided with respect to other types of injectors that serve as containers for fluid agents. Similarly, although reference is made herein in some embodiments to an NFC-chip-enabled injector, such reference is intended to refer to any type of injector (whether it be a BFS vial mechanism, a traditional glass vial or otherwise) that is associated with a unique identifier that is readable via a software app as described herein (e.g., has an NFC chip or RFID chip embedded within it or attached to it in some manner, or a QR code attached to it, that allows a unique identifier of the NFC chip to uniquely identify the corresponding injector and the specific dose of fluid agent contained therein). An injector that has such a unique identifier corresponding to it is also referred to as a Unique ID injector herein. It should be noted that if the term "injector" is used rather than "Unique ID injector", it should not be interpreted to imply that a unique identifier is not associated with that injector in the context described, as the term "injector" is used as a shorthand for "Unique ID injector" in some passages. Further, it should be noted that a unique identifier or data storage mechanism comprising a unique identifier being attached to, embedded in, printed or embossed on or otherwise associated with an injector may comprise the unique identifier or data storage mechanism storing the unique identifier with an injector may, in some embodiments, mean that the unique identifier or data storage mechanism is attached to or otherwise associated with a particular component (e.g., a BFS vial or a label portion of a BFS vial) or packaging of the injector (e.g., an NFC chip may be attached to foil packaging of an injector).

Applicant has recognized that including a data storage mechanism such as an NFC chip with each injector (e.g., having the data storage mechanism within, or attached to or otherwise corresponding to, the injector or component thereof) would allow certain new and useful benefits to be realized, such as: (i) allowing the injector to connect to the Internet of Things (IoT) and/or communicate with remote servers and/or other devices connected to IoT; (ii) enabling a compliance tracking/reward mechanism (e.g., for self-injection situations, multiple-injection regimens or other situations); (iii) allowing a user (whether such user be an injection provider, a patient receiving an injection, or a parent, guardian or other person associated with the patient receiving the injection) of the Unique ID Injectors to use a specially programmed software app on a mobile device or other device (the app having been previously been downloaded onto the device), referred to as an Injection Management App herein, to input data or information into the App and/or to allow the App to read information from the data storage mechanism (and, in some embodiments, to write data to the data storage mechanism, such as if the data storage mechanism comprises an NFC or RFID chip); (iv) allowing for the verifying, authorizing, tracking, confirming and rewarding of administration of fluid agents from the injectors into patients; and (v) allowing for follow-up communications (e.g., text messages or messages output via the Injection Management App) to be output to patients who have received injections from such injectors, such as to remind the patients to self-inject additional doses or to return to a clinic for additional doses, ask about possible adverse reactions, receive confirmations that additional verified or authorized doses have been injected into the patient as recommended, etc.

It should be noted that there may be at least three different types of users involved in the injection of a fluid agent from an NFC-chip-enabled injector: (i) an injection provider such as a healthcare worker; (ii) a patient into whom the fluid agent is injected; and (iii) a guardian (e.g., parent), friend or family member of a patient into whom the fluid agent is being injected (which, in some cases, may be the person in a village with whom the patient shares a mobile device; collectively such persons who may be associated with a patient are referred to as patient liaison herein). Not all of these types of users may be involved in a given injection. In accordance with some embodiments, one or more of these users may access a different platform, portal or version of an Injection Management App (or access different aspects, functionalities or pages of such an App) on their mobile device to facilitate one or more of the embodiments described herein. For example, an injection provider may access and utilize a first version or aspect of an Injection Management App (referred to as a Provider Platform of the Injection Management App) while a patient or patient liaison may access or utilize a second version or aspect of the Injection Management App (referred to as a Patient Platform of the Injection Management App). In some embodiments, the Patient Platform may facilitate the tracking of the vaccines or other fluid agents administered to a particular patient and provide for an online or electronic record of the vaccines or other fluid agents administered to the patient (e.g., a digital receipt of an injection event or an electronic vaccine certificate). In some circumstances, a family may share a mobile device and the app on that mobile device may allow for the tracking of injections for multiple members of that family.

In accordance with some embodiments, the Injection Management App (whether the Provider Platform or the Patient Platform) may allow for communication of data to/from a remote server of a service that provides or manages the Injection Management App and the injection data collected thereby (such service being referred to as an Injection Management Service herein). In some embodiments, the Injection Management Service may be involved with (e.g., control or have a business relationship with an entity that so controls) the manufacturing and/or distribution of the Unique ID Injectors as described herein and store records of Unique ID Injectors that were manufactured in accordance with embodiments described herein and that are to be tracked from the point of manufacture to the point of injection, in accordance with at least some embodiments described herein. In some embodiments, data collected via an Injection Management App may be cached and stored in local memory when the device on which the app is downloaded is not able to communicate with the Injection Management Service (e.g., when the device is not connected to Wi-Fi or does not have a sufficient cellular service connection) and then transfer the data to the Injection Management Service once a sufficient communication connection is established. In accordance with some embodiments, the Injection Management Service may open a record in a database for each Unique ID Injector that is manufactured in accordance with embodiments described herein. In some embodiments, the Injection Management Service may store in that record the unique identifier of the NFC or RFID chip embedded in or attached to the vial in association with other information corresponding to the dose of fluid agent (e.g., time and place of manufacture; batch, lot and/or strip number; type of fluid agent; dosage of fluid agent; expiration date of fluid agent; etc.). Subsequently, when a user (e.g., an injection provider, patient or patient liaison) taps the Unique ID Injector to their mobile device, the Injection Management App may read the unique identifier stored in the data storage mechanism of the injector (e.g., the NFC chip identifier) and communicate with the Injection Management Service to retrieve information associated with the vial/chip in order to (i) verify or authorize the injection (e.g., check that the fluid agent is not expired or is not subject to a recall); (ii) open or create a new record (or update information in an existing data record) to indicate that the dose of fluid agent corresponding to that identifier is being injected, which may also include storing an indication of various new information obtained from the user or based on the tap of the vial to the phone (e.g., time/place of the injection; identifier of a injection provider, if any, providing the injection; identifier of the patient and/or an identifier (e.g., telephone number) of a mobile device associated with the patient), also referred to as an injection event record herein. In some embodiments, the Injection Management Service operates an Injection Management System that comprises one or more servers operable to communicate with user mobile devices that have the Injection Management App installed thereon and are registered devices and/or users of the System. In some embodiments, the Injection Management System utilizes a blockchain type of distributed network of servers for storing the injection event records (e.g., for security purposes).

In some embodiments, in addition to or in lieu of contacting the Injection Management Service to verify or authorize the injection once a user taps the vial to a mobile device on which the Injection Management App is open, the Injection Management App may read information in addition to the chip identifier from the data storage mechanism (e.g., an NFC or RFID chip may store readable data such as expiration date, dosage, type of fluid agent contained in the vial) and use this information to authorize the injection and output to the user that he/she can move forward with the injection.

In accordance with some embodiments in which a Unique ID Injector comprises a BFS vial mechanism, Applicant envisions that the pre-filled BFS vial that is filled with a fluid agent during the BFS manufacturing process described herein may have embedded within its plastic, or otherwise attached to or included within it or on a surface or portion thereof, an NFC chip (the term "embedded" will be used for purposes of brevity but is intended to encompass all manner of attachment, impregnation, embedding or addition to, into or onto the vial, whether it be a BFS vial, another type of plastic vial or a glass vial). In other embodiments, a data storage device (whether an NFC chip, an RFID chip, or other form) may be glued on or otherwise attached to an injector during the manufacturing process (e.g., it may be glued on or otherwise attached underneath a label, on a label portion of the BFS vial).

Turning now to FIG. 1, a block diagram of a system 100 according to some embodiments is shown. In some embodiments, the system 100 may comprise a plurality of node devices 102*a-n*, a network 104, a management device 106, and/or a server device 110. According to some embodiments, any or all of the devices 102*a-n*, 106, 110 may comprise and/or be in communication with a data storage and/or memory device 140-1*a-n*, 140-2. Each node device 102*a-n* may comprise a local memory device 140-1*a-n*, for example, and/or the server device 110 may comprise a network memory device 140-2. As depicted in FIG. 1, any or all of the devices 102*a-n*, 106, 110, 140-1*a-n*, 140-2 (or any combinations thereof) may be in communication via the network 104. In some embodiments, communications between and/or within the devices 102*a-n*, 106, 110, 140-1*a-n*, 140-2 of the system 100 may be utilized to provide and manage a distributed injection events transaction ledger. The server device 110 may, for example, interface with one or more of the node devices 102*a-n* and/or the management device 106 to execute multiple instances of specially-programmed chain code (not depicted) stored in any or all of the memory devices 140-1*a-n*, 140-2 and/or provide a specially-structured interface via which a user participating in an injection event transaction may obtain, verify, and/or modify status information pertaining to an injection event transaction.

Fewer or more components 102*a-n*, 104, 106, 110, 140-1*a-n*, 140-2 and/or various configurations of the depicted components 102*a-n*, 104, 106, 110, 140-1*a-n*, 140-2 may be included in the system 100 without deviating from the scope of embodiments described herein. In some embodiments, the components 102*a-n*, 104, 106, 110, 140-1*a-n*, 140-2 may be similar in configuration and/or functionality to similarly named and/or numbered components as described herein. In some embodiments, the system 100 (and/or portion thereof) may comprise a distributed injection event management program, system, and/or platform programmed and/or otherwise configured to execute, conduct, and/or facilitate the methods described herein, including method 400, and/or portions thereof.

The node devices 102*a-n*, in some embodiments, may comprise any types or configurations of computing, mobile electronic, network, user, and/or communication devices that are or become known or practicable. The node devices 102*a-n* may, for example, comprise one or more electronic devices, such as mobile devices comprising cellular and/or wireless telephones, such as an iPhone® (also manufactured by Apple®, Inc.) or an LG Optimus™ Zone™ 3 smart phone manufactured by LG® Electronics, Inc. of San Diego, CA, and running the Android® operating system from Google®, Inc. of Mountain View, CA In some embodiments, the node devices 102*a-n* may comprise devices owned and/or operated by one or more users, such as patients, injection providers or third parties seeking to confirm information about a particular injection event transaction. According to some embodiments, the node devices 102*a-n* may communicate with the server device 110 via the network 104 to conduct injection verification inquiries and/or processes and/or to record, store, confirm or update information about an injection event (e.g., the fact that a particular patient received a particular dose of a particular fluid agent at a specified date, time and/or location and/or the current vaccination status of a patient (e.g., as a result of having participated in the vaccination event)), in accordance with a distributed chain code execution process as described herein. In accordance with some embodiments, the node devices 102*a-n* may each store an instance of an Injection Management App as described herein, via which users of the node devices 102*a-n* may communicate with an Injection Management System, which may own, control or operate (or have operated on its behalf) the server device 110.

In some embodiments, the node devices 102*a-n* may interface with the server device 110 and/or the management device 106 to effectuate communications (direct or indirect) with one or more other node devices 102*a-n* (such communication not explicitly shown in FIG. 1) operated by other users, for example. In some embodiments, the node devices 102*a-n* may interface with the server device 110 to effectuate communications (direct or indirect) with the management device 106 (such communication also not explicitly shown in FIG. 1). In some embodiments, the node devices 102*a-n* and/or the server device 110 may execute separate instances of a chain code algorithm that cause an injection event transaction ledger to be distributed in an encrypted and verifiable manner. As described herein, for example, the node devices 102*a-n* and/or the server device 110 may communicate with the management device 106 to execute a cryptographic service utilized to securely disseminate an injection event chain code block or payload to a plurality of the node devices 102*a-n*.

The network 104 may, according to some embodiments, comprise a Local Area Network (LAN; wireless and/or wired), cellular telephone, Bluetooth®, Near Field Communication (NFC), and/or Radio Frequency (RF) network with communication links between the server device 110, the node devices 102*a-n*, the management device 106, and/or the memory devices 140-1*a-n*, 140-2. In some embodiments, the network 104 may comprise direct communications links between any or all of the components 102*a-n*, 106, 110, 140-1*a-n*, 140-2 of the system 100. The node devices 102*a-n* may, for example, be directly interfaced or connected to one or more of the server device 110 and/or the management device 106 via one or more wires, cables, wireless links, and/or other network components, such as network components (e.g., communication links) comprising portions of the network 104. In some embodiments, the network 104 may comprise one or many other links or network components other than those depicted in FIG. 1. The node devices 102*a-n* may, for example, be connected to the server device 110 and/or the management device 106 via various cell towers, routers, repeaters, ports, switches, and/ or other network components that comprise the Internet and/or a cellular telephone (and/or Public Switched Telephone Network (PSTN)) network, and which comprise portions of the network 104.

While the network 104 is depicted in FIG. 1 as a single object, the network 104 may comprise any number, type, and/or configuration of networks that is or becomes known or practicable. According to some embodiments, the network 104 may comprise a conglomeration of different sub-networks and/or network components interconnected, directly or indirectly, by the components 102*a-n*, 106, 110, 140-1*a-n*, 140-2 of the system 100. The network 104 may comprise one or more cellular telephone networks with communication links between the node devices 102*a-n* and the server device 110, for example, and/or may comprise the Internet, with communication links between the server device 110 and the management device 106 and/or one or more of the memory devices 140-1*a-n*, 140-2, for example.

The management device 106, in some embodiments, may comprise any type or configuration of a computerized processing device, such as a PC, laptop computer, computer server, database system, and/or other electronic device, devices, or any combination thereof. In some embodiments, the management device 106 may be owned and/or operated by a third-party (i.e., an entity different than any entity owning and/or operating either the node devices 102*a-n* or the server device 110; such as certificate, authentication, and/or cryptographic service provider). The management device 106 may, for example, execute one or more web services that provide for centralized blockchain cryptographic functionality, such as the Hyperledger™ Fabric™ blockchain framework available from The Linux Foundation® of San Francisco, CA In some embodiments, the management device 106 may receive block chain data from one or more of the node devices 102*a-n* and/or the server device 110, may apply a hash algorithm to the received data, and may transmit the encrypted data to each of the node devices 102*a-n* and the server device 110 (e.g., for storage in local copies of a blockchain ledger). According to some embodiments, the management device 106 may comprise a plurality of devices and/or may be associated with a plurality of third-party entities.

In some embodiments, the server device 110 may comprise an electronic and/or computerized controller device, such as a computer server communicatively coupled to interface with the node devices 102*a-n* and/or the management device 106 (directly and/or indirectly). The server device 110 may, for example, comprise one or more PowerEdge™ R830 rack servers manufactured by Dell®, Inc. of Round Rock, TX which may include one or more Twelve-Core Intel® Xeon® E5-4640 v4 electronic processing devices. In some embodiments, the server device 110 may comprise a plurality of processing devices specially-programmed to execute and/or conduct processes that are not practicable without the aid of the server device 110. The server device 110 may, for example, execute one or more coded rules to manage a blockchain ledger for a plurality of injection event transactions, such management permitting real-time injection event status updates and adjustments which would not be capable of being conducted without the benefit of the specially-programmed server device 110. According to some embodiments, the server device may comprise an Injection Management System as described herein, operable to communicate with patients and injection providers via their respective mobile devices (e.g., node devices 102a-n) in order to obtain, update and transmit verifications of data stored in injection event records embodied in the injection event transaction ledger, injection event database or other repository of electronic records indicating injection events being tracked and managed by the Injection Management System.

According to some embodiments, the server device 110 may be located remote from one or more of the node devices 102a-n and/or the management device 106. The server device 110 may also or alternatively comprise a plurality of electronic processing devices located at one or more various sites and/or locations.

According to some embodiments, the server device 110 may store and/or execute specially programmed instructions to operate in accordance with embodiments described herein. The server device 110 may, for example, execute one or more programs, modules, and/or routines that facilitate the management, tracking, authorization, verification and/or updating of injection events, e.g., in an online environment, via an Injection Management App as described herein. According to some embodiments, the server device 110 may comprise a computerized processing device, such as a computer server and/or other electronic device to manage and/or facilitate transactions and/or communications regarding the node devices 102a-n. A private company, government health agency, healthcare company, injector manufacturer and/or other user may, for example, utilize the server device 110 to (i) receive or recognize injection events that are associated with Unique ID injectors, (ii) authorize injections from such injectors, (iii) receive confirmations from injection providers that a dose of a particular fluid agent has been administered to a particular patient (e.g., at a particular date/time and/or location); (iv) store a vaccination status of a particular patient for a particular vaccine as a result of any of the foregoing; and/or (iii) provide an interface via which third parties can confirm a vaccination status of a patient and/or provide updates in real-time, as described herein.

In some embodiments, the node devices 102a-n, the management device 106, and/or the server device 110 may be in communication with the memory devices 140-1a-n, 140-2. The memory devices 140-1a-n, 140-2 may comprise, for example, various databases and/or data storage mediums that may store, for example, injector data, fluid agent data, registered patient data, registered injection provider data, injection event data, and/or injection or vaccination status data obtained from the node devices 102a-n, digital receipt data (including privacy levels associated with digital receipts, in embodiments employing such levels) defined by the server device 110, injection authorization processing rules, chain code instructions, blockchain data, cryptographic keys and/or data, login and/or identity credentials of registered users, and/or instructions that cause various devices (e.g., the server device 110, the management device 106, and/or the node devices 102a-n) to operate in accordance with embodiments described herein.

The memory devices 140-1a-n, 140-2 may store, for example, blockchain data defining a distributed injection event transaction ledger that stores records of injection event transactions (e.g., data defining injection events in which an injection has been authorized and/or administered to a particular patient and an injection provider has provided data indicating that a particular fluid agent has been administered to a particular patient, including attendant details such as the time/date, location, fluid agent and/or injection provider corresponding to the injection), chain code instructions, data that causes communications with the management device 106 (e.g., an API and/or API tunnel to a web service that provides blockchain authentication, certification, and/or cryptographic hashing). In some embodiments, the memory devices 140-1a-n, 140-2 may comprise any type, configuration, and/or quantity of data storage devices that are or become known or practicable. The memory devices 140-1a-n, 140-2 may, for example, comprise an array of optical and/or solid-state hard drives configured to store injection event transaction ledger data provided by (and/or requested by) the node devices 102a-n, injector and/or injection event analysis data (e.g., analysis formulas and/or mathematical models), and/or various operating instructions, drivers, etc. While the memory devices 140-1a-n, 140-2 are depicted as stand-alone components of the various node devices 102a-n and the server 110, the memory devices 140-1a-n, 140-2 may comprise multiple components. In some embodiments, a multi-component memory devices 140-1a-n, 140-2 may be distributed across various devices and/or may comprise remotely dispersed components. Any or all of the node devices 102a-n, the management device 106, and/or the server device 110 may comprise the memory devices 140-1a-n, 140-2 or a portion thereof, for example.

Figure 2:
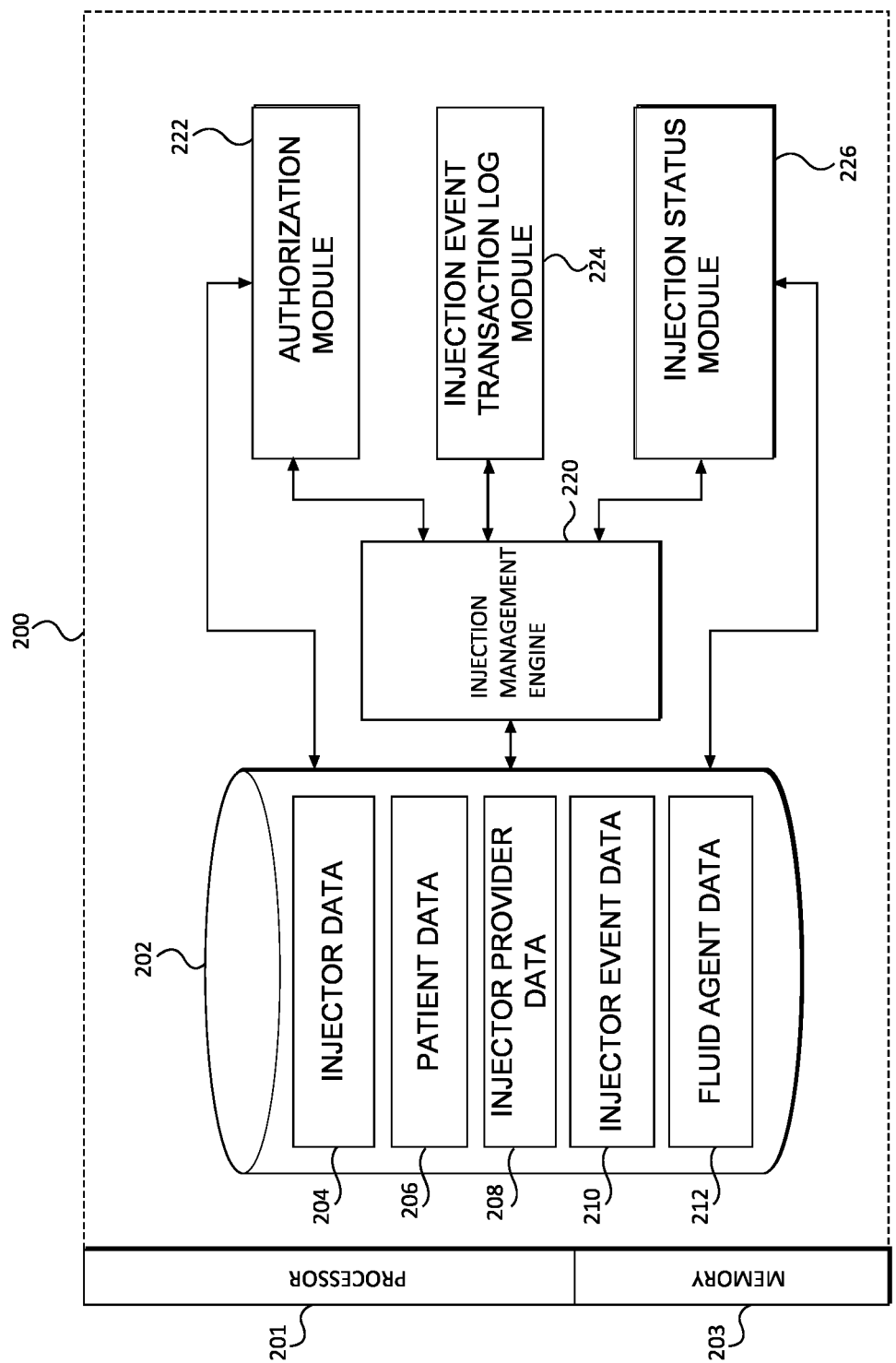
FIG. 2 is an example block diagram of a server device consistent with at least some embodiments described herein.

Turning now to FIG. 2, illustrated therein is a block diagram of an Injection Management System 200 that may be a component of an Injection Management Service as described herein. The Injection Management System 200 may comprise, in one embodiment, an example of server device 110 (FIG. 1). The Injection Management System 200 may comprise, for example, a processor 201, a memory 203, a database 202 and a plurality of software modules 222-226.

In accordance with some embodiments, any or all of the components of the Injection Management System 200 may comprise one or more hardware components, such as microprocessors, microcontrollers, or digital sequential logic, etc., such as processor 201. The processor 201 may comprise one or more processors, such as one or more INTEL™ processors, working sequentially or in parallel. The processor 201 is in communication with, or operatively connected to, a memory 203. The memory 203 may comprise an appropriate combination of magnetic, optical, and/or semiconductor memory, and may include, for example, Random Access Memory (RAM), Read-Only Memory (ROM), a compact disc and/or a hard disk. The processor 201 and the memory 203 may each be, for example: (i) located entirely within a single computer or other device; or (ii) connected to each other by a remote communication medium, such as a serial port cable, telephone line or radio frequency transceiver. In one embodiment, the system 200 may comprise one or more devices that are connected to a remote server computer for maintaining databases or injection event transaction records (e.g., a management device 106 of FIG. 1).

The system 200 may further comprise a database 202, which may in some embodiments store data useful for implementing one or more embodiments described herein, non-limiting examples of which include (i) data associated with one or more users (e.g., patients receiving injections and/or injection providers), (ii) data associated with one or more drug companies whose drugs are packaged in injectors; (iii) data associated with injectors comprising data storage mechanisms storing unique identifiers; (iv) data associated with one or more injection events or injection event transactions; and (v) data associated with one or more rewards earned (or in the process of being earned) by patients on an injection compliance program, as described herein.

In accordance with some embodiments, the database 202 includes data, associated data structures, and database management software. The database 202 may, for example, be implemented using any well-known database management systems, including Microsoft SQL, Oracle, IBM DB2, etc. It should be noted that in some embodiments, database 202 (or at least some of the data described as being stored therein) may be stored in memory 203 and/or in another memory device accessible to the memory 203 and/or to processor 201. For example, in one embodiment database 202 (or at least some of the data described as being stored therein) may be stored in a memory of a third-party server, such as a server of a cloud-based computing service with which the Injection Management Service may contract for purposes of storing data.

In some embodiments, the data described herein as being stored in database 202 may be stored across more than one database; the example data described herein as being useful in at least some embodiments is described as being stored in a single database 202 merely for purposes of simplicity. In accordance with some embodiments, one or more of the types of data 204-212 may be stored as a separate database.

An example of a type of data that may be stored in database 202 includes injector data 204 defining a uniquely identifiable injector (and, in the case of pre-filled injectors, the dose of fluid agent packaged therein) recognized by the system (e.g., injectors which are registered with the system for purposes of being tracked, managed and/or authorized). Such injector data may include at least one of (i) a unique serial number of the injector (which may, in some embodiments, comprise a unique serial number of an NFC or other chip attached to or otherwise associated with the injector); (ii) a batch number for the fluid agent contained in the injector; (iii) a manufacturer's lot identifier of the fluid agent; (iv) a time and/or place of manufacture of the fluid agent and/or the injector; (v) the type, category and/or name of the fluid agent packaged in the injector; (vi) an expiration date of the fluid agent, if any; (vii) a strip ID number (e.g., if injectors are manufactured and distributed in strips of multiple injectors); (viii) a dosage or strength of the fluid agent; (ix) an intended destination or recipient (e.g., child vs. adult); (x) one or more characteristics of the injector (e.g., it is a 1.5 ml BFS vial); and/or (xi) other information desirable for identifying or tracking the Unique ID Injectors and/or the fluid agent contained within it (e.g., recall alerts). In some embodiments, the unique serial number may be a unique identifier that points to other data (e.g., at least some of the information indicated in items (ii)-(x) of the preceding list). In some embodiments, the injector data 204 may be utilized as part of an injection authorization process (e.g., to confirm that the injector is not counterfeit, the dose in it has not bee subject to a recall, etc.).

Another example of a type of data that may be stored in database 202 includes patient data 206 defining patients who have registered with the Injection Management System 200 (e.g., individuals who have downloaded an Injection Management App in order to track their injection events, such as to track the vaccines they have received and their vaccination status for various infectious diseases), in accordance with at least some embodiments described herein. Such patient data 206 may include, in each respective patient record of the patient data 206, at least one of: (i) a name; (ii) contact data; (iii) a unique identifier (e.g., as assigned by the Injection Management System or a third party organization that has partnered with the Injection Management System to help manage injection event information for individuals of that organization); (iv) login credentials (e.g., username and password via which the patient may log into a patient portal of the Injection Management App); (v) health history; and (vi) injection event status or vaccination status for various infectious diseases that the patient has been vaccinated for (or not).

In some embodiments, the Injection Management System may allow for different levels of privacy to be associated with a given digital receipt for an injection event transaction or vaccination. For example, a first version or level of such a digital receipt may allow the patient to remain anonymous while sharing the version of the digital receipt with a third party in order to confirm his/her vaccination status for a particular infectious disease. Such a version or privacy level of the digital receipt may indicate, for example, a status of vaccination of the patient and some information about the vaccination (e.g., time/date and/or place of vaccination) without providing personally identifying information (PII) about the patient). A second version or level of the digital receipt may include PII of the patient. In such embodiments, different permission requirements may correspond to the different privacy levels of the digital receipt (e.g., the patient/user may need to provide an additional password or participate in dual-factor authentication to confirm that the second level, including PII, of the digital receipt is to be shared with a third party. In such embodiments, the different levels of the digital receipt (and, e.g., the different information to be shared with third parties under each) and corresponding permission requirements for each level may also be stored for a patient in the patient's record of the patient data 206.

In some embodiments, data defining a digital receipt for an injection event may be stored in the patient data 206, while in other embodiments an identifier of the digital receipt may be stored in the patient data 206 that points to another location in which the digital receipt is stored (e.g., in the injection event data 210 or another database or ledger of digital receipts that is stored separately from both the patient data 206 and the injection event data 210).

Yet another example of a type of data that may be stored in database 202 includes injection provider data 208 defining individuals who are registered with Injection Management System 200 as injection providers. Such injection provider data may include, for each record of a patient provider, at least one of: (i) a name; (ii) contact data; (iii) a unique identifier (e.g., as assigned by the Injection Management System or a third party that has partnered with the Injection Management System to assist with administering injections to patients via injectors registered with the Injection Management System); and (iv) login credentials (e.g., username and password via which the patient may log into an injection provider portal of the Injection Management App). In some circumstances, a given individual may be registered with the Injection Management System as both a patient and an injection provider, in which case the individual would need to log in to the appropriate portal or platform (patient vs. injection provider) depending on the reasons for logging in.

Yet another example of the data that may be stored in database 202 is injection event data 210 defining a list of injection events or injection event transactions that have been recognized and recorded by the Injection Management System 200. The injection event database may, in some embodiments, comprise an embodiment of a injection event transaction ledger as described with respect to FIG. 1, or represent some or all of the same data as would be stored in the ledger. In accordance with some embodiments, each record of the injection event data 210 may store information defining a particular injection event that was recognized and recorded (e.g., in accordance with a method such as method 400 described with respect to FIG. 4). Examples of the data that may be recorded in injection event data 210 include: (i) a date/time of an injection (it should be noted that the terms "date", "time" and "date/time" are used interchangeably herein to refer to a date and/or time of an event); (ii) the location at which an injection was administered (e.g., based on information provided by an injection provider and/or patient, whether affirmatively by selecting from a list of choices or passively based on GPS or geolocation information obtained from a mobile device of either or both); (iii) an indication or identifier of the injection provider who administered the injection; (iv) an identifier of the patient to whom the injection was administered; (v) an indication of the injection (e.g., an indication of the dose and/or fluid agent that was administered, drug name, batch or lot number, etc.); (vi) an expiration date for the injection, if any; (vii) a unique identifier of an injector utilized in the injection event; (viii) a unique identifier for the transaction (if different from the injector identifier), which may be generated by the Injection Management System 200 upon a new record of injection event data 210 being opened; (ix) a passcode generated once the administration of the injection has been confirmed (e.g., in accordance with the process 400 of FIG. 4), which may expire; (x) an expiration time for the passcode and/or an indication of whether the passcode was received from the patient prior to the expiration time; (xi) a status of the injection corresponding to the injection event (e.g., if the injection is for a vaccine that is effective for a predetermined period of time, the stats may indicate whether the injection is currently considered valid/active vs. expired); and (x) a digital receipt or digital receipt identifier corresponding to the injection event. In some embodiments, data defining a digital receipt for an injection event may be stored in the injection event data, while in other embodiments an identifier of the digital receipt may be stored in the injection event data 210 that points to another location in which the digital receipt is stored (e.g., in the patient data 206 or another database or ledger of digital receipts that is stored separately from both the patient data 206 and the injection event data 210).

Yet another example of the data that may be stored in database 202 is fluid agent data 212. Fluid agent data 212 may comprise data regarding various fluid agents that are packaged in injectors being managed by Injection Management System 200. In some embodiments, an injection provider may be able to look up information about a particular fluid agent pulled from fluid agent data 212 when administering the fluid agent to a patient. In other embodiments, the fluid agent data 212 may be utilized as part of an injection authorization process. Examples of information about a fluid agent that may be stored in fluid agent data 212 include, without limitation: (i) the ailment or disease that the fluid treats/prevents or a name for the fluid agent; (ii) a manufacturer of the fluid agent; (iii) ingredients included in the fluid agent (e.g., for allergy or compatibility purposes); (iv) distributor or contract manufacturer that produced the fluid agent; and (v) contact information for a pharmaceutical company or other representative who may be able to provide additional information about the fluid agent, or for submitting concerns, complaints, questions or problems corresponding to the fluid agent.

It should be noted that the examples provided herein of what type of information may be included in which type of example data should not be taken in a limiting fashion. Modifications can be made as to what type of information is stored with which type of data, different types of data may be combined, some information may be stored with more than one type of data, etc.

The Injection Management System 200 may further comprise one or more software module(s) or engines for directing the processor 201 to perform certain functions. In accordance with some embodiments, software components, applications, routines or sub-routines, or sets of instructions for causing one or more processors to perform certain functions may be referred to as "modules" or "engines" herein. It should be noted that such modules, engine or any other software or computer program referred to herein (including the Injection Management App that can be downloaded to user's mobile devices for facilitating communications with the Injection Management Service, such as via the Injection Management Server 200), may be written in any computer language and may be a portion of a monolithic code base, or may be developed in more discrete code portions, such as is typical in object-oriented computer languages. In addition, the modules, engines or any software or computer program referred to herein, may in some embodiments be distributed across a plurality of computer platforms, servers, terminals, and the like. For example, a given module may be implemented such that the described functions are performed by separate processors and/or computing hardware platforms.

With reference to FIG. 2, it should be understood that any of the software module(s) or computer programs illustrated therein may be part of a single program or integrated into various programs for controlling processor 201. Further, any of the software module(s) or computer programs illustrated therein may be stored in a compressed, uncompiled, and/or encrypted format and include instructions which, when performed by the processor 201, cause the processor 201 to operate in accordance with at least some of the methods described herein. Of course, additional and/or different software module(s) or computer programs may be included and it should be understood that the example software module(s) illustrated and described with respect to FIG. 2 are not necessary in any embodiments. Use of the term "module" or "engine" is not intended to imply that the functionality described with reference thereto is embodied as a stand-alone or independently functioning program or application. While in some embodiments functionality described with respect to a particular module may be independently functioning, in other embodiments such functionality is described with reference to a particular module for ease or convenience of description only and such functionality may in fact be a part of integrated into another module, program, application, or set of instructions for directing a processor of a computing device.

According to an embodiment, the instructions of any or all of the software module(s), engines or programs described with respect to FIG. 2 may be read into a main memory from another computer-readable medium, such from a ROM to RAM. Execution of sequences of the instructions in the software module(s), engines or programs causes processor 201 to perform at least some of the process steps described herein. In alternate embodiments, hard-wired circuitry may be used in place of, or in combination with, software instructions for implementation of the processes of the embodiments described herein. Thus, the embodiments described herein are not limited to any specific combination of hardware and software. Some non-limiting examples of software module(s) that may be utilized in system 200 include: (i) an injection management engine 220; (ii) an authorization module 222; (iii) an injection event transaction log module 224; and (iv) an injection status module 226.

In the example embodiment illustrated in FIG. 2, the injection management engine is illustrated as communicating with (i) a an authorization module 222; (ii) an injection event transaction log module 224; (iii) an injection status module 226; and (iv) the database 202. Thus, the injection management engine is operably to access the data in the database 202 and, either itself or by providing such data to one or more of the modules 222-226, perform some of the functionalities and embodiments described herein. Such an arrangement is illustrated as one example of how the data in database 202 may be accessed, modified and utilized.

Generally, the injection management engine 220 and the modules 222-226 should be understood as being accessible to processor 201, irrespective of how in particular they are arranged within the system 200, to implement one or more embodiments described herein. As described, one or more of the engine 220 and the modules 222-226 may be operable to utilize at least some of the data stored in database 202. Further, in accordance with some embodiments, one or more of the engine 220 and the modules 222-226 may be operable to retrieve, manipulate, select, update, modify and/or determine data that is transmitted to and stored in database 202.

Injection management engine 220 may, in accordance with some embodiments, operate to manipulate the data from database 202 in order to perform or facilitate one of the following example functionalities: (i) authorize an injection from a uniquely identifiable injector (e.g., based on information received from an injection provider via an injection provider portal of the Injection Management App on the injection provider's mobile device (e.g., a node device 102*a-n* of FIG. 1)); (ii) store a record of each injection or dose of a fluid agent that has been administered by an injection provider utilizing the Injection Management System 200; (iii) generate a digital receipt or other indication of an injection having been administered to a particular patient, to be output to the patient via the patient's mobile device (e.g., a node device 102*a-n* of FIG. 1); and/or (iv) allow a patient who has received an injection or dose of a fluid agent managed by Injection Management System 200 to provide verification of having received the injection or dose in an efficient, electronic, secure and verifiable manner.

In accordance with one embodiment, the injection management engine 220 or another component of system 200 may be operable to output information to a user such as a patient or injection provider registered with the system 200 (and receive input or data from such users, such as an injector identifier, information confirming that an injection has been successfully administered or a passcode for finalizing verification that the injection has been successfully administered) via one or more graphical user interfaces (GUIs) of an Injection Management App as described herein. Examples of such GUIs are described herein with reference to FIGS. 3A-3L. An example of a process via which information may be received from, or output to, users such as injection providers and patients, is described herein with reference to FIG. 4.

The interfaces of an Injection Management App may, for example, take the form of a Web server that conveys data in HTML, XML, or other well-known formats using well-known transmission protocols, such as HTTP and TCP/IP. Proprietary protocols and data formats may also be used. FIGS. 3A-3L illustrate non-limiting examples of the type of information that may be output to, and mechanisms which may be collected from, a user via an Injection Management App operable to interface with Injection Management System 200.

Figures 3A, 3B:
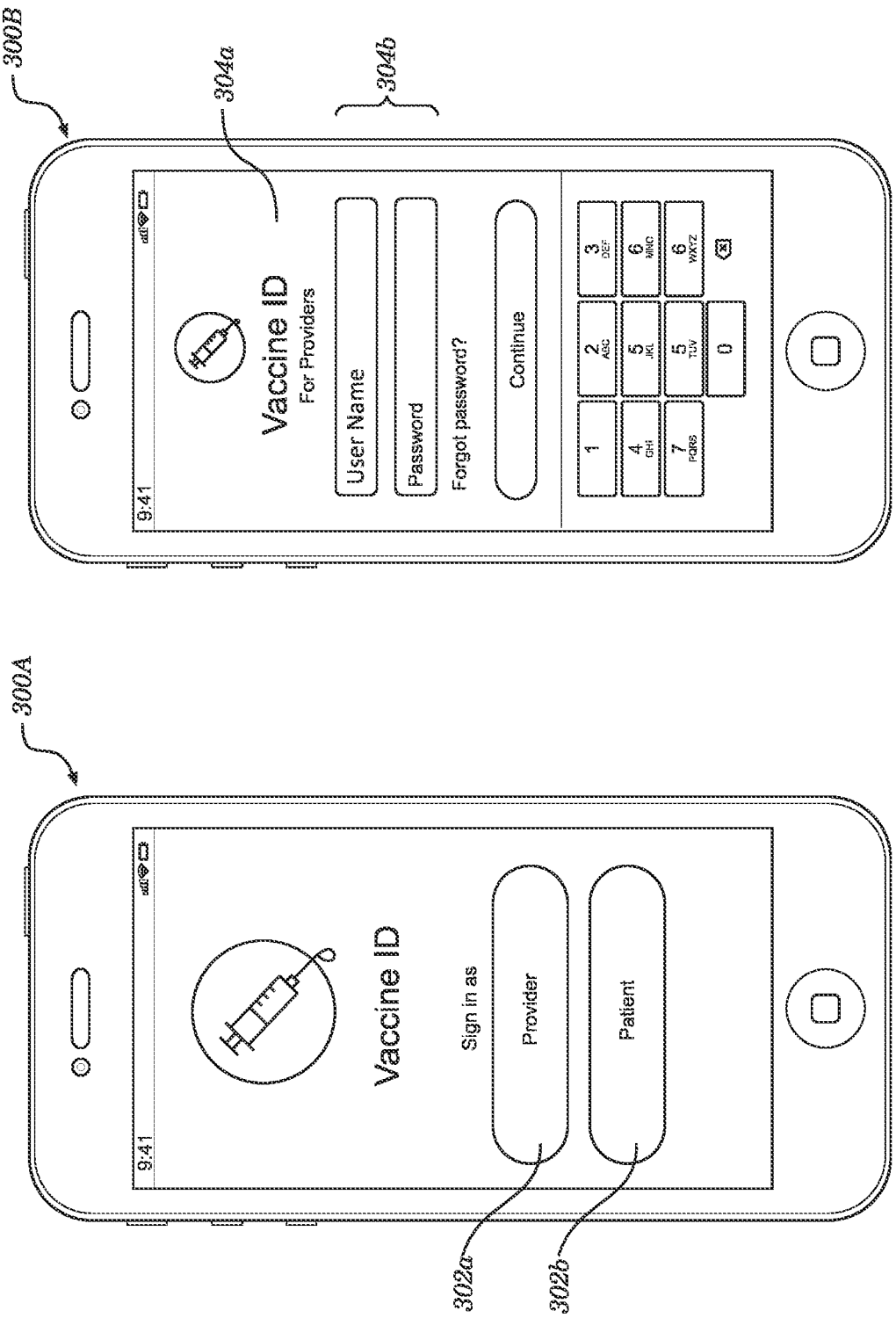
Figure 3H:
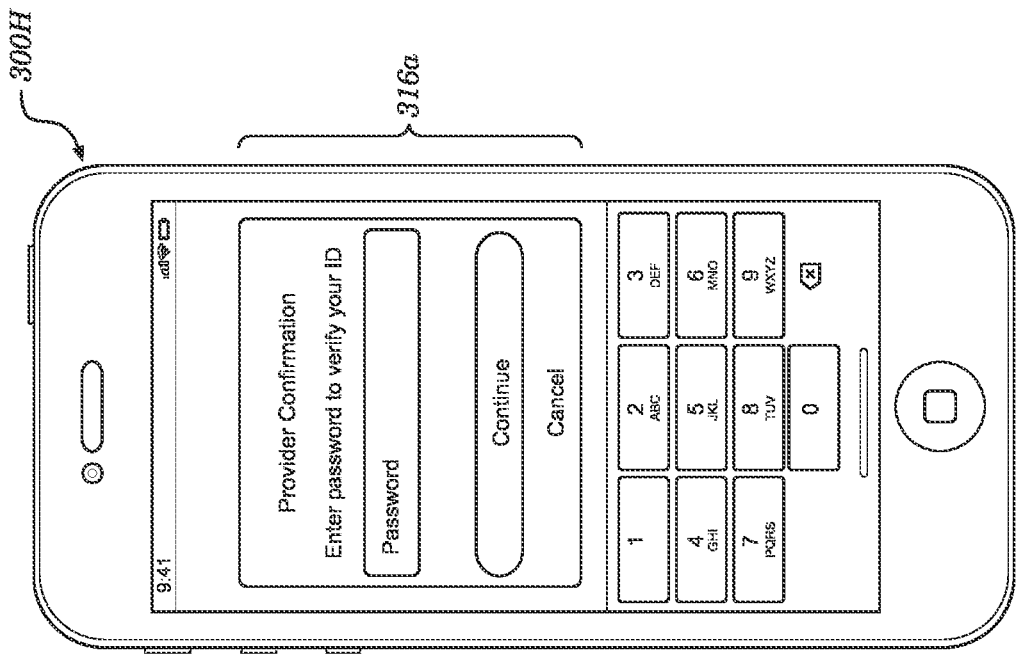
Figure 3G:
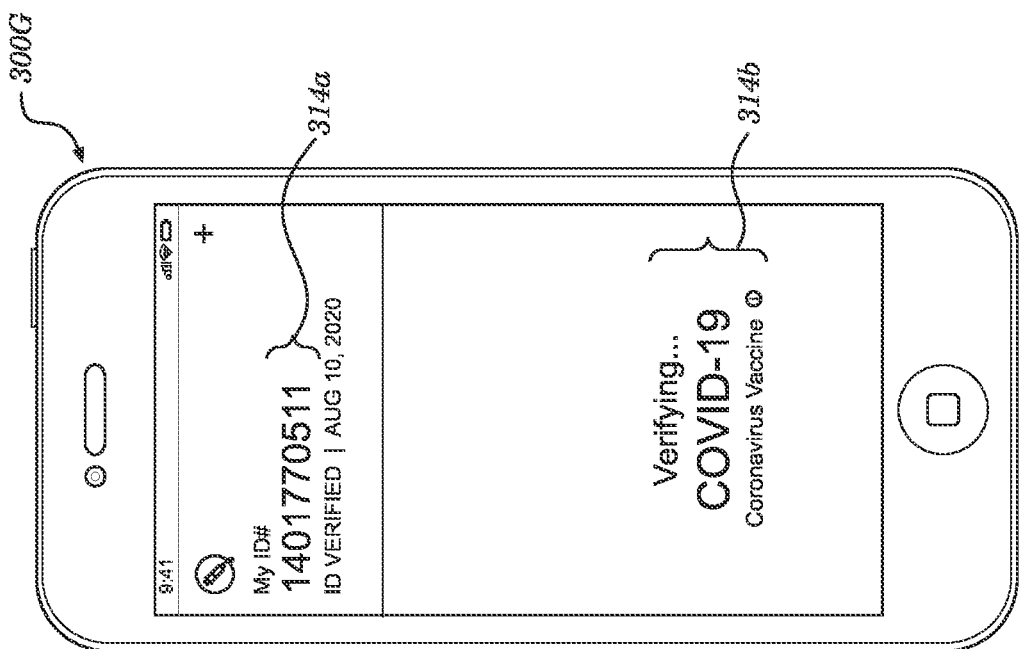
Figure 3K:
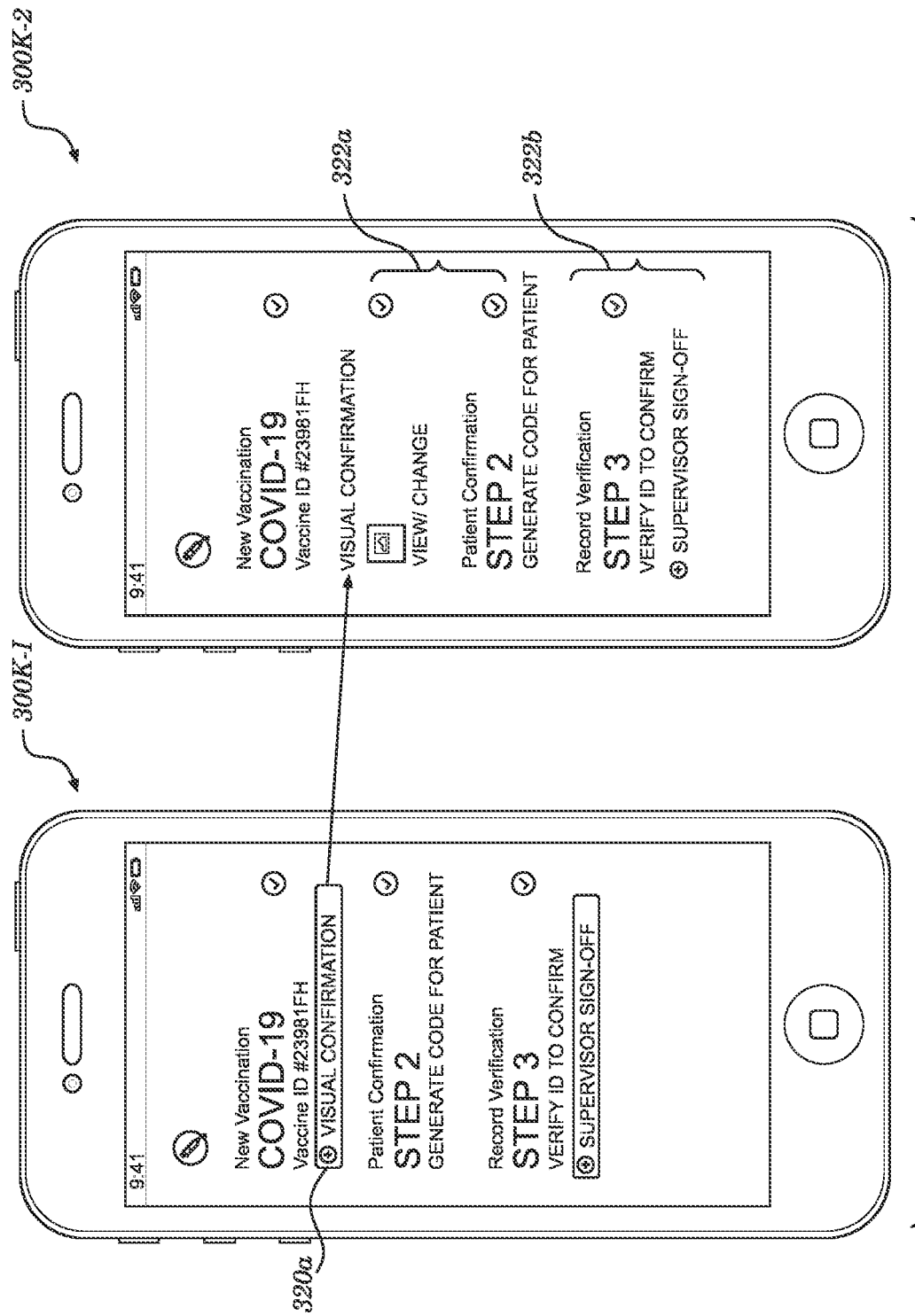
Figure 3L:
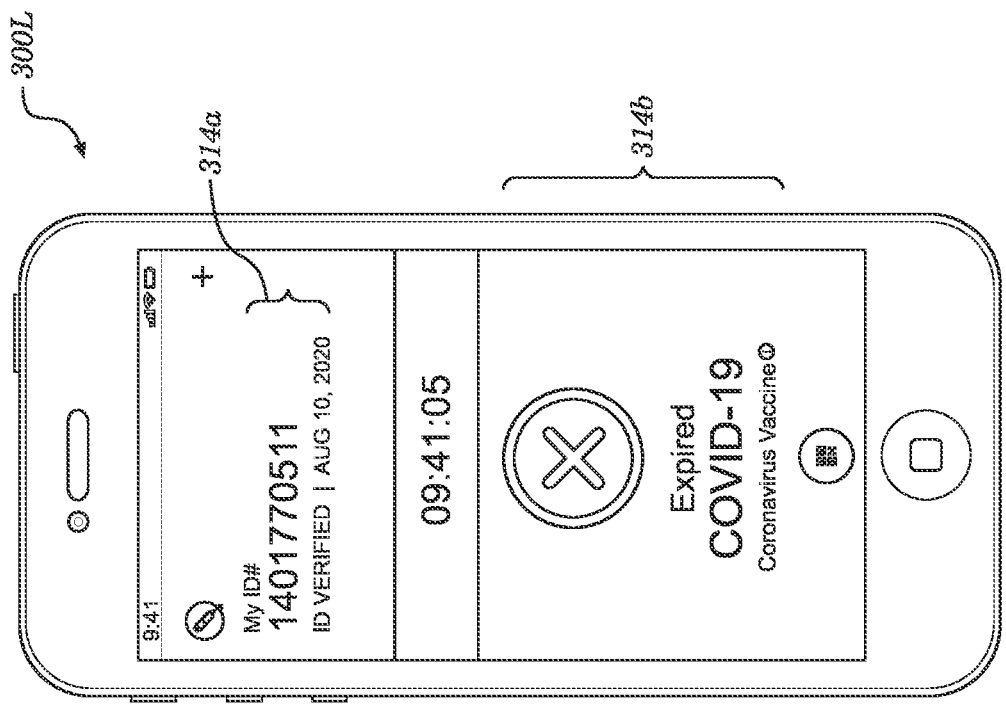
Figure 4:
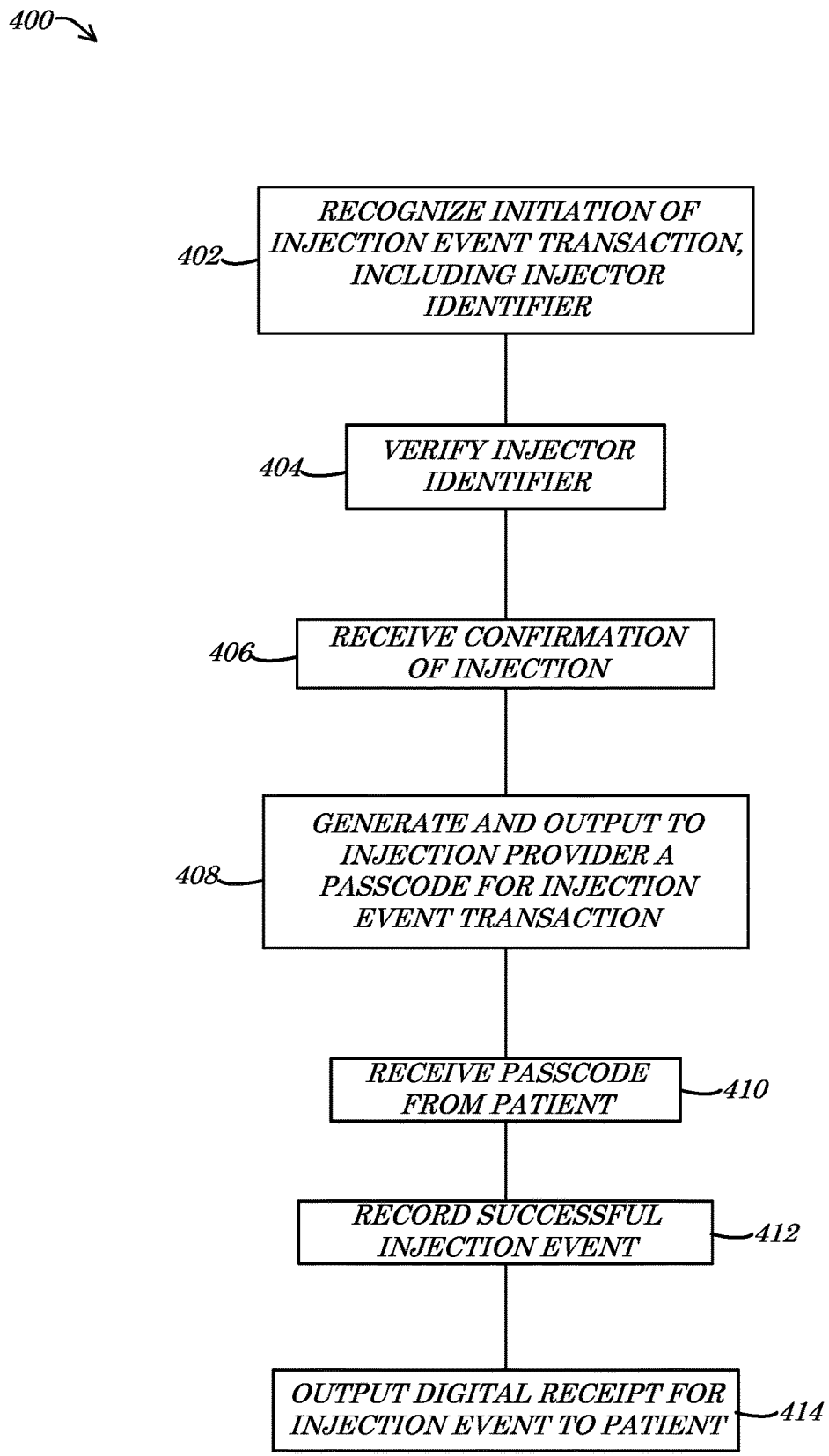
FIG. 4 is an example process flow diagram of an example process consistent with at least some embodiments described herein.

Turning now to FIGS. 3A-3L and FIG. 4, illustrated in FIG. 4 is an example process 400 which provides one embodiment of some functionality of an Injection Management System as described herein, with reference to FIGS. 3A-3L for example GUIs that may be utilized in such a process. Process 400 may, for example, be performed by Injection Management System 200 (FIG. 2). In some embodiments, the process 400 may be performed and/or implemented by and/or otherwise associated with one or more specialized and/or specially-programmed computers (e.g., the processor 201 of FIG. 2). It should be noted, with respect to process 400 and all other processes described herein, that not all steps described with respect to the process are necessary in all embodiments, that the steps may be performed in a different order in some embodiments and that additional or substitute steps may be utilized in some embodiments.

Process 400 is described herein with reference to FIGS. 3A-3L, which illustrate a plurality of example GUIs (not to be taken in any limiting fashion) which may be presented to a user (in some cases an injection provider and in some cases a patient, as described herein) during a progression of an injection event transaction. FIGS. 3A-3L each illustrate a respective GUI as it may be output on a mobile device of a respective user (which may comprise an example of a node device 102*a*-102*n* of FIG. 1). The GUIs of FIGS. 3A-3L may comprise several tabs, screens or pages of an App (software application operable to run on a mobile device), or particular version, portal or platform thereof (e.g., some screens are those from an injection provider portal that is output when a user signs in as an injection provider while other screens are those from a patient portal that is output when a user signs in as a patient). It should be noted that many variations on such graphical user interfaces may be implemented (e.g., menus and arrangements of elements may be modified, additional graphics and functionality may be added). The graphical user interfaces of FIGS. 3A-3L are presented in simplified form in order to focus on particular embodiments and features being described.

Turning now to FIG. 3A, illustrated therein is a GUI 300A that may be output via mobile device to a user who has an Injection Management App installed on their mobile device. This may be the sign-in screen that is presented to a user each time the Injection Management App is launched or opened. In accordance with one embodiment, the App may comprise different portals/platforms for different types of users, such as patients and injection providers. In such embodiments, a user may first be prompted to select whether he/she is signing in as an injection provider (in which case the user would select the option depicted by area 302*a* of the GUI 300A) or a patient (in which case the user would select the option depicted by area 302*b* of the GUI 300A). In other embodiments, different Apps may be available to different users such that a given user may only launch the App corresponding to his/her role (e.g., injection providers may have access to a first App while patients may have access to a second App, such that there is not a need to select a type of user on the launch screen). It is presumed, for purposes of describing the embodiments depicted via FIGS. 3A-3L, that users who are injection providers and users who are patients have previously registered with the Injection Management System 200 and are thus recognized by the Injection Management System (e.g., have data stored corresponding to them in the patient data 206 and/or the injection provider data 208 of the example system 200 of FIG. 2) and have sign-on credentials that are recognized by the System 200 (a registration process via which such users can register with the System should be understood by one of ordinary skill in the art and is not described herein, for purposes of brevity).

Turning now to FIG. 3B, illustrated therein is an example GUI 300B that may be presented to a user who is an injection provider (as indicated in area 304a of GUI 300B). In order to proceed with using the Injection Management App and access functionality of the Injection Management Service as described herein, a user provides his/her user name and password, or other credentials as desired by the Injection Management Service. In some embodiments, the user name may be a unique identifier assigned to the user (e.g., by the Injection Management Service or a third party organization that has partnered with the Injection Management Service to help its members or participants manage their injection events). In some embodiments, additional security measures may be incorporated to verify the identity of the user signing in to the Injection Management App (e.g., dual factor authentication).

Turning now to FIG. 3C, illustrated therein is an example GUI 300C that may be output to an injection provider to indicate the process (and current status of where the process currently stands) for an injection event transaction. An injection event may be considered to be the event during which a patient has an injection (a dose of a fluid agent) administered to him/her (e.g., an event comprising a patient receiving a dose of a specific vaccine). An injection event transaction is activity participated in by the patient receiving an injection and the Injection Management Service (or the injection provider, as a representative of the Injection Management Service), in which activity the patient receives the injection, and a digital receipt thereof, in exchange for providing information that allows the Injection Management Service to track and store a record of the patient having received the injection (e.g., a unique identifier that allows the System 200 to identify the patient and a passcode that allows the System to confirm that the patient had a dose of a particular fluid agent administered to him/her via a Unique ID injector, as described herein). Recording the transaction, in accordance with embodiments described herein, allows both the patient and the Injection Management System to subsequently access and verify the occurrence of the injection event in an efficient and secure manner.

As illustrated in FIG. 3C, in accordance with some embodiments, the process for an injection event transaction may include (i) registering the injection of a dose of a fluid agent (referred to as "Register a Vaccination" and Step 1 in area 306a, assuming the fluid agent in the example of FIGS. 3A-3L is a vaccine); (ii) receiving a confirmation from the patient of the fluid agent having been administered to the patient (referred to as "Patient Confirmation" and Step 2 in area 306a); and (iii) storing a verifiable record of the injection event (referred to as "Record Verification" and Step 3 in area 306a). The description of process 400 herein, with reference to FIG. 4, provides some example manners in which each step in such a process may be implemented.

In accordance with some embodiments, as each step of this example process is completed, the injection provider's app will show an indication of the successful completion of the step (e.g., as shown via a checkmark or other visual aid). Although the particular example screen of GUI 300C illustrates checkmarks next to each of the steps, it may be assumed that until a given step has been confirmed, the step would be indicated as incomplete (e.g., with no checkmark next to it, by appearing grayed out, or via some other visual aid).

Turning now to FIG. 4, process 400 is initiated at block 402 upon an initiation of an injection event transaction being recognized by the system (e.g., Injection Management System 200), which comprises receiving an injector identifier. In some embodiments, a patient identifier or other patient check-in process may precede block 402 (e.g., the injection provider or an associate thereof may first process the patient through a standard appointment check-in process before the injection event begins in substance).

An initiation of an injection event transaction may be recognized, for example, based on a unique injector identifier being received from an injection provider via the Injection Management App. An example of a GUI or interface via which an injection provider may transmit or provide a unique injector identifier is illustrated in FIG. 3D as GUI 300D. As described herein, each injector management by an Injection Management Service may be equipped with, or correspond to, a data storage mechanism such as an NFC chip, RFID chip, QR code, bar code or other mechanism via which a sensor of a mobile device on which the Injection Management App is installed, and such data storage mechanism may store a unique identifier that uniquely identifies the injector. In accordance with the embodiments illustrated in FIG. 3D, the data storage mechanism is an NFC chip and thus an injection provider may be prompted to input the unique identifier of an injector the injection provider is about to use to administer an injection to a patient by holding the injector close to the injection provider's mobile device or by tapping the injector (or a specific part of the injector, such as a label area in which the NFC chip is located) to the mobile device. In embodiments in which the data storage mechanism comprises something other than an NFC chip, the user may be prompted in a different manner to input the unique injector identifier, as appropriate. For example, the user may be prompted to scan a QR code or bar code on the injector or hold the injector comprising an RFID chip in close proximity to an RFID antenna that is operable to read the information from the RFID chip (which antenna may, in turn, be in communication with the injection provider's mobile device and/or Injection Management System in order to transmit the unique identifier of the injector and allow the injection event transaction to proceed).

Once the injection event transaction is initiated and the unique injector identifier is received in block 404, the injector identifier is verified (e.g., as being authentic) and the corresponding injector is authorized for use. For example, information associated with the injector identifier may be retrieved and an authorization process may be performed (e.g., to confirm that the injector is not expired, previously used, subject to a recall and/or otherwise not authorized for use). In accordance with some embodiments, the functionality described with respect to block 404 may be carried out at least partly by authorization module 222 (FIG. 2).

In one embodiment, once the injector identifier is received in block 404, it is used to access data associated with the injector (as described with respect to FIG. 2). For example, a record of injector data 204 may be accessed by the Injection Management System 200 and one or more fields may be reviewed by a program or module (e.g., authorization module 222) to confirm that there are no existing conditions that would cause the injector to not be authorized for use by the injection provider (e.g., that the injector is not subject to a recall; that the injector is authentic, which it may be presumed to be if the injector identifier is found in the injector data). In some embodiments, the Injection Management System may output information about the injector and/or fluid agent packaged in the injector to the injection provider via a GUI (not shown), as part of the injector authorization process. For example, the injection provider may be prompted to confirm that certain information printed or embossed on the injector or a label thereof matches information as stored in a database in association with the injector identifier provided by the injection provider.

In accordance with some embodiments, additional information or considerations may be involved in verifying an injector identifier and whether it the injector should be authorized for use (i.e., block 404 may comprise additional steps and/or authorization module 222 may perform additional verifications). For example, in some embodiments, a BFS vial or other type of injector may include a vaccine vial monitor (VVM) which may comprise an environmental monitoring mechanism (e.g., a strip adhered to the injector). In accordance with some embodiments, a VVM comprises a thermochromic label put on vials containing vaccines or other fluid agents which gives a visual indication of whether the vaccine or other fluid agent has been maintained within a temperature range which preserves its potency. The labels were designed in response to the problem of delivering vaccines to developing countries where environmental characteristics (e.g., the heat or cold within which the vaccines are stored) were difficult to maintain and track and where formerly vaccines were being rendered inactive and administered ineffectively due to having been denatured by exposure to inappropriate temperatures (e.g., temperatures that are too cold for the vaccines). In some embodiments, the VVM may comprise a measure of a cumulative amount of heat or cold that the vial to which it is attached was exposed since it left the manufacturing facility. The label may turn black if the vial is exposed to an unacceptable temperature for an unacceptable period of time, a black label indicating that the vaccine or other fluid agent within the vial is no longer good and thus should not be injected. In other embodiments, a more expensive digital VVM may be utilized to track similar ambient temperature information.

In accordance with some embodiments in which an injector may include VVMs, an NFC chip or other component of the injector may comprise an optical chip monitor which allows for reading the output of a VVM (e.g., whether the VVM label has turned black). For example, a user may open the appropriate Injection Management App on their mobile device and tap the vial comprising the NFC chip and/or optical chip monitor to their mobile device (hold their mobile device (or camera of their mobile device) over the VVM) such that the app can read an indication of whether the vaccine is good and may be used, based on the VVM output. In another example, the user may open the appropriate Injection Management App on their mobile device and take a photo of the VVM output and the App may be programmed (or a server comprising a processor operable to implement an appropriate program, with which the App is in communication, may be so programmed) to determine, based on the output of the VVM, whether the fluid agent in the vial is good for use. In either example, if the Injection Management App determines based on the VVM output that the fluid agent is good to use, it may output to the user an indication that the user is authorized to inject the fluid agent (e.g., a green button, light or other indicator may appear in a screen of the Injection Management App), as described above with respect to otherwise authorizing an injector for use and providing an indication of such authorization to the injection provider. In one example, Applicant envisions a simple optical monitor included with/in the vial and operable to communicate with, or monitor the status of, the VVM such that if the VVM label (or indicator of a digital VVM) turns black (or otherwise indicates the fluid agent has been exposed to unacceptable temperatures), that causes a signal or determination that the fluid agent is no longer viable or authorized for use. The optical monitor may then be operable to communicate this indication to the NFC chip and/or the Injection Management App, and causes the NFC chip and/or the Injection Management App to determine that the fluid agent in the vial should not be authorized for injection into a patient.

Once the injector is authenticated by verifying the injector identifier as authentic and determining that there is no other information known to the Injection Management System that would cause the injector to not be authorized for use, the injection may be considered registered or verified. This may comprise, for example, generating a record for the injection event transaction (e.g., opening a new record for the current injection event transaction in a database of the Injection Management System 200 (e.g., in injection event data 210 of FIG. 2) and/or generating a unique transaction identifier for the injection event transaction). Further, once the injector is authenticated and authorized for use, Step 1 of the process illustrated in FIG. 3C may be considered to have been completed and a visual indication of this may be output to the injection provider via the GUI 300C (e.g., a checkmark may be output next to Step 1, or Step 2 may be highlighted or become activated). In some embodiments, additional visual, audio and/or tactile indications may be output to the injection provider to indicate that the injector has been authorized for use and that the injection provider should proceed with administering the injection to the patient (e.g., a symbol or other visual indication (e.g., checkmark, green light or thumbs up or completed circle), sound or vibration may be output via a GUI of the Injection Management App).

If the injector identifier is not successfully verified or the Injection Management System 200 determines that the injection is not authorized, an error, warning or other message indicating a failure to authorize the injection may be output to the injection provider via a GUI of the Injection Management App. For example, the injection provider may receive an indication that a recall has been issued for the injector (in which case the injection provider may attempt to verify a different injector and discard the rejected injector) or that the read of the injector identifier was invalid (in which case the injection provider may try to tap the injector to the mobile device again, scan the QR or other code again, or otherwise re-try to input the injector identifier, such as manually typing in a human-readable code of the injector).

Assuming an injection identifier is successfully verified and an injection of a fluid agent packaged therein is authorized for use in block 404, the system awaits for the injection provider to provide an indication that the dose of the fluid agent corresponding to the injector identified in block 402 has been administered to a patient. It should be noted that in some embodiments, at this point in the process, the system may not have identified the patient to whom the injection is to be administered while in other embodiments a patient identifier may have been provided for the injection event transaction record (e.g., by the injection provider or by the patient). Once the system has received a confirmation (e.g., from the injection provider) that the injection has been successfully administered to a patient (block 406), a unique passcode is generated and output to the injection provider via a GUI of the Injection Management App (block 408). An example of such a passcode being output to an injection provider is illustrated in the example of GUI 300E (FIG. 3E). Although area 310a of GUI 300E illustrates a six-digit numeric passcode, any length or type of passcode may be utilized.

The passcode generated by the system (either locally by a module of the Injection Management App or remotely by a server device, such as server device 110, with which the user's mobile device is communicating by means of the Injection Management App) for purposes of being communicated to the patient who has received the injection, such that the patient can use the passcode to validate his/her presence at the injection event and further provide a data to the Injection Management System as part of the injection event transaction. In some embodiments, the injection provider may show or read aloud the passcode to the patient, as output in the injection provider's mobile device. In some embodiments, the passcode may be output in the form of a QR code or other mechanism that is readable directly by the patient's mobile device.

In some embodiments, the passcode may correspond to an expiration time, such that the passcode is only valid until the expiration time. In some embodiments, a new passcode may be generated based on a request from the injection provider if more time is needed for the patient to receive and utilize the passcode. In some embodiments, the generated passcode is stored in association with the injection event transaction (e.g., in injection event data 210 and/or an injection event transaction ledger, if different). The generated passcode may, in some embodiments, be transmitted to devices other than the injection provider's mobile device. For example, in some embodiments the passcode may be transmitted (e.g., texted) directly to a patient based on contact information previously stored in association with an identifier of the patient provided earlier in the process pertaining to the injection event. In another example, the passcode may be transmitted to another server device (e.g., management device 106 of FIG. 1).

Once the passcode is generated in block 408, Step 2 of the process illustrated in FIG. 3C may be considered completed and a visual or other indication of this completion may be output to the injection provider via the injection provider portal of the Injection Management App (e.g., GUI 300E may be updated to indicate completion of Step 2). Once the passcode is output, the system awaits an input of the passcode from the patient.

In accordance with some embodiments, upon arriving at an appointment for an injection event, a patient may sign in to the patient portal of an Injection Management App (e.g., by selecting the "patient" option in area 302b of GUI 300A and then inputting the appropriate sign-in credentials in area 304b of GUI 300B). Upon signing in to the Injection Management App (and, in some embodiments, after selecting the appropriate "injection confirmation" option of the App), the patient may be prompted to input a passcode as provided by an injection provider after an injection is administered to the patient. An example GUI 300F (FIG. 3F) illustrates one example interface via which a patient may be so prompted to enter a passcode. The patient may proceed to confirm that he/she received the injection by providing the passcode vi area 312a of GUI 300F. In some embodiments, the patient may also be prompted to provide other information relevant to the injection event transaction (e.g., to confirm a time/date, location of the injection and/or fluid agent that was administered to the patient). Once the passcode (and any other confirming information or input) is received from the patient (block 410), the system may record a successful injection event as having been completed (block 412).

In some embodiments, additional steps or input by the injection provider may need to be performed in order for the system to consider the injection event verified and determine the injection event transaction to be successfully verified and/or completed. For example, in some embodiments, after the passcode is received from the patient device, the injection provider may be prompted (via the Injection Provider App of the injection provider's mobile device) to re-enter his/her password in order to confirm his/her identity and "sign off" on the injection as having been successfully completed. FIG. 3H illustrates an example GUI 300H in which the injection provider is prompted to enter a password or other credentials via area 316a to verify the injection. In accordance with some embodiments, this entry of a password or other credentials by the injection provider may serve as a digital "signing" of the injection event record by the injection provider. Other methods for allowing the injection provider to "sign" the injection event record may include having the injection provider input a code via a token or NFC chip on an item provided to the injection provider for this purpose (e.g., the NFC chip or other mechanism of such an item may be operable to communicate a unique identifier to the Injection Management App for purposes of confirming the injection provider's presence and identity). In some embodiments, such a token or other item may likewise be utilized by the injection provider to sign in to the injection provider portal of the Injection Management App.

Receiving a successful confirmation or verification from the injection provider for the injection record, after receiving the passcode from the patient, may serve to satisfy Step 3 of the Injection Management App process as indicated in example GUI 300C. The injection provider may further, in some embodiments, be prompted to affirmatively confirm a successful completion of an injection event by selecting a "save" or similar option via the Injection Management App, such as illustrated in area 318a of example GUI 300I of FIG. 3I. Allowing the injection provider to affirmatively "save" the injection event and indicate it as finished may also provide the system to have the injection provider review and confirm other information the system has gathered about the injection event for the injection event transaction record, by outputting it to the injection event provider (e.g., as also illustrated in the example GUI 300I).

In some embodiments, the system may also confirm the passcode entered by the patient into the patient portal of the Injection Management App by determining that (i) the passcode received from the patient in block 410 matches the passcode output to the injection provider in block 412); and (i) the passcode was received prior to an expiration time of the passcode. While the system is verifying the passcode as entered by the patient (and, in some embodiments, awaiting the injection provider's input that serves as a "signing" of the injection event record), the patient's Injection Management App may output an indication of the pending verification status (e.g., as illustrated in the area 314b of the example GUI 300G, FIG. 3G). Once the verification process has been completed (e.g., based on the injection provider providing data to sign off on the injection event (e.g., providing a password or other code or input to confirm the injection provider's identity) and, in some embodiments, additionally indicating that the injection event is complete, the patient's Injection Management app may output an updated status for the injection event or injection (e.g., a status of "Vaccinated" if the injection is a vaccine, as well as a name of the vaccine and/or the infectious disease against which the patient has been vaccinated). The example GUI 300J of FIG. 3J illustrates one manner in which such an updated status may be output to the patient.

It should be noted that some or all of the functions described herein with respect to blocks 402-412 may be performed by authorization module 222 (FIG. 2) and/or injection event transaction log module 224 (FIG. 2). For example, the injection event transaction log module 224 may serve to update or transmit updates regarding an injection event transaction to another device (e.g., node devices 102*a-n* and/or management device 106) in order to enable that device to update its records for the injection event transaction while the authorization module 222 may serve to perform functions that allow such updates/data to be confirmed or verified.

In some embodiments, receiving the passcode from the patient in block 412 may also serve to identify and/or confirm the identity of the patient who is participating in the injection event transaction. For example, in some embodiments, the passcode received from the patient via the patient portal of the Injection Management App may be received in a data packet that also includes an indication of a unique identifier of the patient (e.g., as received as a result of the patient signing in to the patient portal of the Injection Management App in order to enter the passcode so that it can be provided to the system via the App and as indicated in area 314*a* of GUI 300G). The system, based on matching the passcode received from the patient to a passcode that was generated and output to an injection provider as part of an open injection event transaction, may identify the patient and add an indication of the patient identifier to the injection event transaction record for the transaction. In some embodiments, updating the injection event transaction record with the patient identifier may be done as part of the process of block 412.

In some embodiments, once an injection event is completed and the transaction considered to be successfully recorded (block 412) in one or more records, additional data in the form of a digital receipt for the injection event may be generated and transmitted to the patient's mobile device (step 414). In some embodiments, it is the transmission of such data/digital receipt that allows the patient portal of the Injection Management App to display a "vaccinated" or similar status to indicate that the patient has received an injection of the corresponding fluid agent. In some embodiments, digital receipt may include data such as an effective date or expiration date for the injection. For example, in some circumstances an injection may not be considered effective until some period of time (e.g., two (2) weeks) after the patient receives the injection. In another example, an injection may only be effective for some period of time (e.g., one (1) year)). In such cases, the digital receipt may be self-executing for such data in that the status of the injection or patient with respect to the injection (e.g., a vaccination status of the patient for a particular vaccine) may automatically be updated in the Injection Management App based on a comparison of a current time to an effective time and/or expiration time for the injection. For example, if the injection is only valid or effective for one (1) year after having been administered to the patient, when the patient logs into the patient portal of the Injection Management App at a time after the effective time, the status of the injection may show as "Expired" or something similar. An example of such a status and how it may be displayed for a particular vaccine is illustrated in GUI 300L of FIG. 3L.

As described herein, in some embodiments the Injection Management System may allow for different levels of privacy to be associated with a given digital receipt for an injection event transaction or vaccination. For example, a first version or level of such a digital receipt may allow the patient to remain anonymous while sharing the version of the digital receipt with a third party in order to confirm his/her vaccination status for a particular infectious disease. Such a version or privacy level of the digital receipt may indicate, for example, a status of vaccination of the patient and some information about the vaccination (e.g., time/date and/or place of vaccination) without providing personally identifying information (PII) about the patient). A second version or level of the digital receipt may include PII of the patient. In such embodiments, different permission requirements may correspond to the different privacy levels of the digital receipt (e.g., the patient/user may need to provide an additional password or participate in dual-factor authentication to confirm that the second level, including PII, of the digital receipt is to be shared with a third party. In such embodiments, the different levels of the digital receipt (and, e.g., the different information to be shared with third parties under each) and corresponding permission requirements for each level may also be stored for a patient in the patient's record of the patient data 206. In some embodiments, public-private key encryption may be employed to allow the patient to control release of certain private information associated with the digital receipt for an injection.

In some embodiments, the Injection Management System may output a code (e.g., a QR code) or other means via which a patient can share or "flip" a verification that the patient is currently vaccinated against a particular infectious disease or otherwise has received a particular fluid agent. The injection status module 226 (FIG. 2) may function to (i) track and update the status of a patient vis-à-vis injections of particular fluid agents; and (ii) generate codes or permissions via which the patient may share his/her injection status with third parties (e.g., accept permission requirements or decryption passwords from the patient and release the digital receipt or certain levels or data of the digital receipt to authorized third parties).

In some embodiments, the Injection Management System 200 may require additional information or data to be provided by in the injection provider during an injection event before considering the injection event transaction to be completed and verified. In one example embodiment, the system may prompt the injection provider to take a photo or video of the patient who is receiving the injection and upload it as part of the injection event confirmation process (e.g., in block 406) or prior to considering an injection event transaction successfully recorded (e.g., in block 412). The example of FIG. 300K illustrates one implementation of such an embodiment. In this example, GUI 300K-1 of the injection provider portal prompts the injection provider, via area 320*a*, to upload a visual confirmation of the patient's presence and image and GUI 300K-2 illustrates the visual confirmation as having been uploaded as part of the patient confirmation process in area 322*a*.

In some embodiments, a supervisor or other second person in addition to the injection provider may be required to confirm an injection event prior to it being completed. The example embodiment illustrated in FIG. 3K also illustrates how such an embodiment might be implemented, by providing for an input mechanism of a supervisor's sign-off (as part of Step 3 in GUI 300K-1 and in area 322*b* of GUI 300K-2).

In accordance with some embodiments, an NFC or RFID chip may be read-only chip while in other embodiments it may further be a writable chip to which information may be added. In some embodiments, the NFC or RFID chip may be a passive chip such that it does not include its own power source and may be powered by a reader device (e.g., a user's mobile phone) or other mechanism that is outside the NFC chip.

In embodiments in which the NFC or RFID chip is a writable chip (and perhaps other embodiments), there may be a need for a power supply or source for the chip. In one embodiment, a power source or supply may be included in an injector. In one embodiment, the power source may be embedded in a BFS vial (e.g., a capacitor may be embedded in the BFS vial as part of the extrusion process). Other examples of sources or supplies of power that may be used to provide power to a NFC or RFID chip include, without limitation: (i) power created by a user from squeezing or pressing the BFS vial in order to inject the fluid agent within the vial; (ii) power created by a user shaking the BFS vial; (iii) power from a light or solar source included on/in the BFS vial; (iv) by use of piezoelectric effect and/or materials; (v) power from an external light, either natural as in sunlight, or by holding the device under a bright light source (e.g., in a plastic vial embodiment, the plastic of the vial could be embedded with a solar conversion chemical or material, wherein having the vial in the light provides a very low microvolt trickle charge to an associated battery or capacitor). It should be understood that in many embodiments, the amount of power needed for many of the embodiments described herein (if power for the NFC or RFID chip is needed at all) may be very small (e.g., one or two microvolts or even a fraction of a microvolt).

In accordance with some embodiments, an NFC or RFID chip may become faulty, run out of power, become damaged, or rendered at least partially inoperable such that information on it cannot be rewritten or such that additional information cannot be written to it or stored within it. In some embodiments, an NFC or RFID chip may have limited capabilities (e.g., it can only be written to or rewritten a maximum number of times or within a maximum period of time). Thus, it may be desirable in some embodiments for an NFC or RFID chip to have the capability of confirming that the information that a user is attempting to write to it, or rewrite on it, has been successfully written or processed. Any and all of the information that is communicated to/from an NFC or RFID chip may, in at least some embodiments, be encrypted or secured or include a secure element, such that it is protected from unauthorized access.

In accordance with some embodiments, an NFC or RFID chip may include or provide GPS or location tracking capabilities. For example, the NFC or RFID chip may output or communicate the GPS coordinates of its location (e.g., periodically, non-periodically, in response to being interrogated by a sensor or in response to another condition being satisfied). In some embodiments, the GPS or location tracking functionality may provide for the NFC or RFID chip to determine and/or store (or provide information to allow another device, such as a user's mobile device using a corresponding software app to determine and/or store) information such as a current or past location of the vial corresponding to the NFC or RFID chip (e.g., where it has been and how long it has been there, where it currently is).

In accordance with some embodiments, the functionality of each NFC or RFID chip may be tested during the manufacturing process after it is embedded into the BFS vial, and any vials that are determined to include NFC chips that are not functionality properly or within desirable parameters may be discarded or routed to a specialized handling process. Thus, in one embodiment, the manufacturing process may provide for (i) adding an NFC or RFID chip to the vial (e.g., embedding the NFC or RFID chip into the plastic in a plastic extrusion manufacturing process or attaching the NFC or RFID chip under the cap of a glass vial or to another portion of a glass vial); (ii) filling the vial with the fluid agent and sealing it; (iii) testing the NFC or RFID chip to determine whether it is functioning within acceptable parameters (e.g., testing whether the unique identifier stored on it can be read successfully); and (iv) performing one of (a) allowing the vial to proceed to a first manufacturing pathway (e.g., to be packaged and sold as an unique ID injector) if the NFC or RFID chip is tested successfully or (b) routing the vial to a second manufacturing pathway (e.g., to be discarded or to be sold as a non-NFC chip vial) if the NFC chip is not tested successfully). In accordance with some embodiments, an inkjet or other printer may also print an indication of the NFC or RFID chip identifier of an NFC or RFID chip embedded in, or attached to, a vial or component of a vial. The indication may be in human readable form (e.g., an alphanumeric code) or in machine readable form (e.g., a bar code or QR code). The indication may be printed directly on the vial or component of the vial (e.g., a cap, in the case of a glass vial) or onto a label that is then put on the vial. Thus, in such embodiments, the manufacturing process described above may further provide for (v) reading the NFC or RFID identifier of the NFC or RFID chip embedded in the vial; and (vi) causing a printing mechanism to print the NFC or RFID identifier and place it on the vial (either directly or as a label that is put on the vial).

In accordance with some embodiments, use of an Unique ID injector by a user in conjunction with an Injection Management App provides for a user (e.g., a patient into whom the fluid agent of the vial is injected) to be rewarded for a qualifying use (self-injecting the vaccine/medicine in the vial once it is authorized by the app and during an appropriate window of time). In one embodiment, an end user (a user who will be self-injecting the vaccine/medicine in the injector) downloads an Injection Management App onto his smart phone as a pre-requisite for allowing the user to earn rewards (e.g., extra minutes for phone use, extra data for a data plan, monetary payments, etc.) based on qualifying use of the vial (in other embodiments the user need not have the app downloaded and an off-line method for verifying the use may be implemented). For example, the user can earn extra phone minutes by tapping the vial to the smart phone (after opening up the app) during a qualifying window of time (e.g., during a time at which the user is supposed to be self-inject the vaccine/medicine in the injector based on a treatment regimen stored in the app). If the user taps the injector during a qualifying window, the user earns extra phone minutes or another reward (in some embodiments the injection may also additionally need to be authorized by the app based on information such as a verification that the dose in the injector is not expired or the VVM status of the injector is acceptable, as described herein).

In some embodiments in which a user is prescribed a multi-injection regimen, a reward value may be based on how well a user complies with a multi-injection regimen. For example, for certain diseases or conditions a user may need to self-inject multiple doses at specific intervals. In such a circumstance a user may be rewarded based on a "completion game": the user will be provided with a relatively with a relatively large reward upon complying with all of the required injections but a smaller reward if he/she only complies with some but not all of the injections.

Thus, in accordance with some embodiments, the Injection Management Service can effectively assign a unique identifier to a specific dose of a fluid agent (e.g., a specific dose of a vaccine) at the point of manufacture/filling of the injector, in a manner that does not readily allow a modification of the relationship between the dose and the unique identifier of the NFC or RFID chip that is embedded in or attached to the injector in which the dose is stored. This allows many benefits, including a tracking of when/where a particular dose of a fluid agent is injected into a patient and allowing a injection provider to readily verify that the dose in the injector about to be injected is in fact what it purports to be (e.g., by using the Injection Management App to read the unique identifier of the NFC or RFID chip of the injector prior to injection and having the app verify/authorize the dose for use).

In some embodiments, an NFC or RFID chip may be operable to provide for periodic, non-periodic (e.g., triggered by certain events or on a random basis) or continuous GPS tracking history of the location of the chip/injector (e.g., stored on the chip (e.g., in the cloud, on a server with which the NFC or RFID chip and/or a mobile device on which the Injection Management App is downloaded is operable to communicate). Additionally, the chip may communicate with a VVM, store a photo or indication of a status of a VVM or what otherwise be operable to determine a status of a VVM. This VVM status data can be stored locally on the chip and/or in another location (e.g., in the cloud and/or on a server with which the NFC or RFID chip and/or a mobile device on which the Injection Management App is downloaded is operable to communicate). Thus, in accordance with some embodiments, the NFC or RFID chip can know, with respect to the injector and the does of fluid agent it contains, one or more of: (i) where it is now, (ii) where it's been; (iii) what temperatures it has been exposed to over its long journey; and (iv) how long it's been since the day it was made and how much time has elapsed since then.

In accordance with some embodiments, a Injection Management App (via the NFC chip) and/or the NFC or RFID chip itself may be operable to recognize, store and/or forward to a server or other device various data that may be provided by a user, whether a injection provider, patient or other user. For example, as described herein, a user who is injecting a fluid agent from an NFC or RFID chip-enabled injector into a patient or a user who self-injecting the fluid agent may tap the vial to his/her mobile device prior to performing the injection such that data from the NFC or RFID chip is read and processed by the app. For example, the app may verify (based on information about the patient known to the app) that (i) the injector contains the appropriate fluid agent; (ii) it is being administered during an appropriate time; and (iii) the fluid agent is still good to inject (e.g., the VVM does not indicate that it has been exposed to inappropriate temperatures, an expiration date associated with the injector does not indicate the fluid agent is expired, there are no recalls associated with the vial, the vial is not a stolen vial, etc.). In some embodiments, the user may be requested to take a picture of the vial and/or the injection site at the time of the injection (in some embodiments the user may be rewarded for providing this information). In some embodiments, the user may be requested to provide an indication of side effects or reactions to the fluid agent (e.g., by answering one or more questions and/or uploading a picture of the injection site or the relevant side effect) using the app (and in some embodiments the user may be rewarded for providing such information).

In accordance with some embodiments, a user may be rewarded with phone minutes or mobile payments for providing certain information to the app or complying with certain injection requirements that the app is tracking (e.g., by following an injection regiment, such as for a diabetes or TB medical treatment, as prescribed). Examples of such reward include, without limitation, phone minutes and mobile payments (e.g., micropayments). Such rewards may be provided to individual users (E.g., the patient) or a group of users (e.g., to a family account for the family associated with the mobile device on which the app is stored).

In accordance with some embodiments, a Injection Management App may be utilized to communicate or follow up with users (e.g., patients who received injections or guardians or family members thereof). For example, a text message or app reminder may be sent to the mobile device of a user, reminding the user to take another self-injection of a fluid agent in accordance with a regiment. In another example, a text message or app reminder may prompt the user provide an indication of any reaction or side effect to an injection.

It should be noted that in some circumstances a user may be reluctant to receive text messages or reminders that make it clear that the messages or reminders are for an injection, or which specify the type of injection/fluid agent that the user needs to inject. For example, the user may be embarrassed for others to see these types of messages or reminders (which may be particularly problematic of the user is receiving the reminders or messages on a shared family mobile device). Thus, in some embodiments, the messages or reminders may be cloaked or coded such that they do not explicitly say that they are about an injection or what injection they are referring to.

In accordance with some embodiments, and particularly in the case of self-injections by users who are not injection providers, it may be desirable to know how much of the fluid agent in an injector was actually injected into a patient. Thus, for example, a comparison of a refractive index before and after the injection may be taken and reported using the Injection Management App. In another example, a flow meter at the valve level (of the one-way valve in the delivery mechanism) may be compared before and after the injection to determine an amount of fluid agent that was delivered.

In accordance with some embodiments, it may be desirable to verify that the injection of the fluid agent in the Unique ID Injectors was indeed injected into a person or at least an animal (e.g., and not merely squeezed out into the air in order to obtain a reward associated with the injection). Thus for example, a measure of back pressure at the time of the injection may be taken and/or a picture of the injection site taken at or around the time of the injection may be required to be input to the app.

In accordance with some embodiments, the functionality or operability of a one-way valve that comprises a delivery mechanism that is attached to the NFC or RFID chip enabled injector may be controlled or affected by the NFC or RFID chip. For example, in accordance with some embodiments (e.g., as a measure of preventing injection of fluid agents contained in NFC or RFID chip-enabled injectors that have been stolen), the one-way value may only be opened and the fluid agent thus allowed to flow out if the Unique ID Injectors is first tapped to a mobile device on which the Injection Management App is open and the app verifies that the injector is authorized and not stolen or otherwise unsuitable for use. Only if the app verifies the authorized use of the injector will it send a communication to the NFC or RFID chip or another component of the injector (e.g., a gate or obstacle associated with the valve), allowing the valve to open.

In accordance with some embodiments (e.g., embodiments in which the NFC or RFID chip or another component of the injector allows for 2-way communication) the injector may be operable to broadcast its position (e.g., periodically or non-periodically), such as its current GPS coordinates. In some embodiments, the NFC or RFID chip or other component of the injector may be operable to make a phone call or text if it determines that it is in an unauthorized or unexpected location or simply to communicate its location. In yet another embodiment, the NFC or RFID chip or other component may be remotely interrogated when necessary to determine its location. All of the foregoing may help prevent or track down stolen injectors.

It should be noted that although it has been described herein that compliant or authorized injections from an Unique ID Injectors may be tracked via an app on a user's mobile device, a mobile device is not required for any embodiments described herein. Alternate devices may be used to help track the user's injections (e.g., the user may be provided with a SIM card or other electronic card that is operable to either store an indication of the user's injections directly or store an identifier that points to a cloud-based database which stores an indication of the user's injections).

Rules of Interpretation

Numerous embodiments have been described, and are presented for illustrative purposes only. The described embodiments are not intended to be limiting in any sense. The invention is widely applicable to numerous embodiments, as is readily apparent from the disclosure herein. These embodiments are described in sufficient detail to enable those skilled in the art to practice the invention, and it is to be understood that other embodiments may be utilized and that structural, logical, software, electrical and other changes may be made without departing from the scope of the present invention. Accordingly, those skilled in the art will recognize that the present invention may be practiced with various modifications and alterations. Although particular features of the present invention may be described with reference to one or more particular embodiments or figures that form a part of the present disclosure, and in which are shown, by way of illustration, specific embodiments of the invention, it should be understood that such features are not limited to usage in the one or more particular embodiments or figures with reference to which they are described. The present disclosure is thus neither a literal description of all embodiments of the invention nor a listing of features of the invention that must be present in all embodiments.

The terms "an embodiment", "embodiment", "embodiments", "the embodiment", "the embodiments", "an embodiment", "some embodiments", "an example embodiment", "at least one embodiment", "one or more embodiments" and "one embodiment" mean "one or more (but not necessarily all) embodiments of the present invention(s)" unless expressly specified otherwise.

The terms "including", "comprising" and variations thereof mean "including but not limited to", unless expressly specified otherwise.

The term "consisting of" and variations thereof mean "including and limited to", unless expressly specified otherwise.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The term "comprising at least one of" followed by a listing of items does not imply that a component or subcomponent from each item in the list is required. Rather, it means that one or more of the items listed may comprise the item specified. For example, if it is said "wherein A comprises at least one of: a, b and c" it is meant that (i) A may comprise a, (ii) A may comprise b, (iii) A may comprise c, (iv) A may comprise a and b, (v) A may comprise a and c, (vi) A may comprise b and c, or (vii) A may comprise a, b and c.

The terms "a", "an" and "the" mean "one or more", unless expressly specified otherwise.

The term "based on" means "based at least on", unless expressly specified otherwise.

The methods described herein (regardless of whether they are referred to as methods, processes, algorithms, calculations, and the like) inherently include one or more steps. Therefore, all references to a "step" or "steps" of such a method have antecedent basis in the mere recitation of the term 'method' or a like term. Accordingly, any reference in a claim to a 'step' or 'steps' of a method is deemed to have sufficient antecedent basis.

Headings of sections provided in this document and the title are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required, or that each of the disclosed components must communicate with every other component. On the contrary a variety of optional components are described to illustrate the wide variety of possible embodiments of the present invention.

Further, although process steps, method steps, algorithms or the like may be described in a sequential order, such processes, methods and algorithms may be configured to work in alternate orders. In other words, any sequence or order of steps that may be described in this document does not, in and of itself, indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

It will be readily apparent that the various methods and algorithms described herein may be implemented by, e.g., appropriately programmed general purpose computers and computing devices. Typically a processor (e.g., a microprocessor or controller device) will receive instructions from a memory or like storage device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory. Volatile media may include dynamic random access memory (DRAM), which typically constitutes the main memory. Transmission media may include coaxial cables, copper wire and fiber optics, including the wires or other pathways that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Transmission Control Protocol, Internet Protocol (TCP/IP), Wi-Fi, Bluetooth, TDMA, CDMA, and 3G.

Where databases are described, it will be understood by one of ordinary skill in the art that (i) alternative database structures to those described may be readily employed, and (ii) other memory structures besides databases may be readily employed. Any schematic illustrations and accompanying descriptions of any sample databases presented herein are illustrative arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, other formats (including relational databases, object-based models and/or distributed databases) could be used to store and manipulate the data types described herein.

Likewise, object methods or behaviors of a database can be used to implement the processes of the present invention.

In addition, the databases may, in a known manner, be stored locally or remotely from a device that accesses data in such a database.

For example, as an example alternative to a database structure for storing information, a hierarchical electronic file folder structure may be used. A program may then be used to access the appropriate information in an appropriate file folder in the hierarchy based on a file path named in the program.

It should also be understood that, to the extent that any term recited in the claims is referred to elsewhere in this document in a manner consistent with a single meaning, that is done for the sake of clarity only, and it is not intended that any such term be so restricted, by implication or otherwise, to that single meaning.

In a claim, a limitation of the claim which includes the phrase "means for" or the phrase "step for" means that 35 U.S.C. § 112, paragraph 6, applies to that limitation.

In a claim, a limitation of the claim which does not include the phrase "means for" or the phrase "step for" means that 35 U.S.C. § 112, paragraph 6 does not apply to that limitation, regardless of whether that limitation recites a function without recitation of structure, material or acts for performing that function. For example, in a claim, the mere use of the phrase "step of" or the phrase "steps of" in referring to one or more steps of the claim or of another claim does not mean that 35 U.S.C. § 112, paragraph 6, applies to that step(s).

With respect to a means or a step for performing a specified function in accordance with 35 U.S.C. § 112, paragraph 6, the corresponding structure, material or acts described in the specification, and equivalents thereof, may perform additional functions as well as the specified function.

Computers, processors, computing devices and like products are structures that can perform a wide variety of functions. Such products can be operable to perform a specified function by executing one or more programs, such as a program stored in a memory device of that product or in a memory device which that product accesses. Unless expressly specified otherwise, such a program need not be based on any particular algorithm, such as any particular algorithm that might be disclosed in the present application. It is well known to one of ordinary skill in the art that a specified function may be implemented via different algorithms, and any of a number of different algorithms would be a mere design choice for carrying out the specified function.

Therefore, with respect to a means or a step for performing a specified function in accordance with 35 U.S.C. § 112, paragraph 6, structure corresponding to a specified function includes any product programmed to perform the specified function. Such structure includes programmed products which perform the function, regardless of whether such product is programmed with (i) a disclosed algorithm for performing the function, (ii) an algorithm that is similar to a disclosed algorithm, or (iii) a different algorithm for performing the function.

While various embodiments have been described herein, it should be understood that the scope of the present invention is not limited to the particular embodiments explicitly described. Many other variations and embodiments would be understood by one of ordinary skill in the art upon reading the present description.

What is claimed is:

1. A method, comprising:
recognizing, by an electronic processing device of an injection management system, a first injection event transaction,
wherein the recognizing is based on receiving, via an injection provider platform of an Injection Management App stored on a first mobile device corresponding to first user, an indication of a dose of a fluid agent to be administered to a patient, the indication including first data comprising a unique identifier of an injector containing the dose,
wherein the first user previously signed in to the injection provider platform via the first mobile device by providing first user credentials that allowed the electronic processing device to uniquely identify the first user and recognize the first user as a registered injection provider;
authorizing, based on the unique identifier of the injector, the dose of the fluid agent;
generating an electronic record unique to the first injection event transaction, thereby generating a first injection event record;
receiving, from the first user and via the Injection Management App, an indication that the dose has been administered to the patient;
generating, in response to the receiving, a first passcode, the first passcode corresponding to an expiration time of the first passcode and being stored in association with the first injection event record;
outputting the first passcode to the first user via the Injection Management App;
receiving, from a second user and prior to the expiration time, the first passcode,
wherein the second user has previously signed in to a patient platform of the Injection Management App via a second mobile device by providing second user credentials that allowed the electronic processing device to uniquely identify the second user and recognize the second user as a registered patient;
concluding, based on the receiving of the first passcode from the second user, that the second user is the patient to whom the dose of the fluid agent from the injector has been administered by the first user as part of the first injection event transaction;
updating the first injection event record to indicate that the dose of the fluid agent has been administered to the second user; and
transmitting to the second mobile device of the second user, via the patient portal of the Injection Management App, a verifiable confirmation that the dose of the fluid agent has been administered to the second user, thereby transmitting to the second mobile device a digital receipt for the first injection event, to be stored in the patient portal of the Injection Management App of the second user.

2. The method of claim 1, wherein the digital receipt comprises a unique digital receipt identifier that corresponds to the first injection event record, the unique digital receipt identifier for enabling the second user, via the patient portal of the Injection Management App, to communicate with the Injection Management System and verify a vaccination status of the second user based on data stored in the first injection event record.

3. The method of claim 1, further comprising:
outputting, prior to receiving and via the Injection Management App and to the first user, an indication that the injection has been authorized.

4. The method of claim 1, wherein the first injection event record is stored as a blockchain record in a distributed network of the injection management system.

5. The method of claim 1, wherein the digital receipt comprises at least one of the following: (i) an indication of the fluid agent; (ii) an identifier of the injector; (iii) a time of the administration of the dose; (iv) a location of the administration of the dose; (v) an identifier of the second user; and (vi) an indication of the first user who administered the dose.

6. The method of claim 5, wherein the digital receipt includes a code that can, upon request of the second user, be displayed on the second user's mobile device via a GUI of the patient platform of the Injection Management App, the code being readable by an external electronic device in order to confirm that the dose of the fluid agent has been administered to the second user.

7. The method of claim 5, wherein the digital receipt comprises multiple privacy levels of information that can be shared with third parties, each privacy level of information corresponding to a respective permission requirement of the second user, such that in order for a given privacy level of information of the digital receipt to be shared with a third party, the second user must first provide a corresponding permission requirement.

8. The method of claim 7, wherein a first level of information of the multiple levels of information corresponds to anonymous information about the dose administered to the second user without identifying the second user and a second level of information of the multiple levels of information corresponds to information that identifies the second user as well as information about the dose administered to the second user.

9. The method of claim 1:
wherein the fluid agent comprises a vaccine against a particular transmittable disease that is effective for a predetermined period of time from a time of administration, such that the second user is to be considered vaccinated against the particular transmittable disease for the predetermined period of time,
further wherein the digital receipt further comprises an expiration date of the dose that is based on the predetermined period of time, the expiration date for utilization by the patient portal of the Injection Management App, only up to a time of the expiration date, to output via a GUI of the Injection Management App, a confirmation that the second user is considered vaccinated against the particular transmittable disease.

10. The method of claim 1, wherein receiving the indication that the dose has been administered to the patient comprises receiving a photo of the second user taken during the first injection event transaction, and wherein updating the electronic record comprises transmitting a copy of the photo to the second user's mobile device, to be stored in association with the digital receipt.

11. The method of claim 1, wherein a copy of the photo is stored in association with the first injection event record.

12. The method of claim 1, further comprising:
retrieving, based on the unique identifier of the injector and from a database accessible to the electronic processing device, information descriptive of the fluid agent and the dose.

13. The method of claim 12, wherein authorizing comprises:
confirming, based on the information, that the dose is valid and approved for administration.

* * * * *